(12) United States Patent
Carpentier

(10) Patent No.: US 6,338,740 B1
(45) Date of Patent: Jan. 15, 2002

(54) FLEXIBLE HEART VALVE LEAFLETS

(75) Inventor: Alain F. Carpentier, Paris (FR)

(73) Assignee: Edwards Lifesciences Corporation, Irvine, CA (US)

(*) Notice: Subject to any disclaimer, the term of this patent is extended or adjusted under 35 U.S.C. 154(b) by 0 days.

(21) Appl. No.: 09/491,990

(22) Filed: Jan. 26, 2000

Related U.S. Application Data

(63) Continuation-in-part of application No. 09/332,759, filed on Jun. 14, 1999.
(60) Provisional application No. 60/117,445, filed on Jan. 26, 1999.

(51) Int. Cl.$^7$ ................................. A61F 2/06; A61F 9/00
(52) U.S. Cl. ........................ 623/2.13; 623/212; 623/904
(58) Field of Search .................... 623/1.26, 2.1, 623/2.12, 2.13, 2.14, 2.17, 2.18, 904, 910, 929

(56) References Cited

U.S. PATENT DOCUMENTS

| | | |
|---|---|---|
| 4,291,420 A | 9/1981 | Reul |
| 4,451,936 A | 6/1984 | Carpentier et al. |
| 5,147,391 A | 9/1992 | Lane |
| 5,258,023 A * | 11/1993 | Reger ........................ 623/2.18 |
| 5,449,384 A | 9/1995 | Johnson |
| 5,489,297 A | 2/1996 | Duran |
| 5,702,368 A * | 12/1997 | Stevens et al. ..... 604/170.03 X |
| 5,861,028 A | 1/1999 | Angell |
| 5,964,770 A * | 10/1999 | Flomenblit et al. ........... 606/78 |
| 5,895,420 A | 4/2000 | Mirsch, II et al. |
| 6,074,419 A | 6/2000 | Healy et al. |

FOREIGN PATENT DOCUMENTS

| | | |
|---|---|---|
| WO | WO 00/00107 | 1/2000 |

* cited by examiner

*Primary Examiner*—Bruce Snow
*Assistant Examiner*—Brian E Pellegrino
(74) *Attorney, Agent, or Firm*—Debra D. Condino; John Christopher James; Guy L. Cumberbatch

(57) ABSTRACT

A heart valve with a structural stent and radially moveable cusps and commissures. The stent may be of three separate elements, each having a cusp portion and two commissure portions. The commissures may be pivotally or flexibly coupled, and may separate into independent leaflets. A connecting band may be provided that follows the cusps and commissures and extend outwardly. The valve may be connected to the natural tissue along the undulating connecting band. A multi-legged holder having legs alternating between each cusp and commissure may be used for implantation. A method of implantation is also disclosed, as is a system for implanting independent valve leaflets in the native annulus.

25 Claims, 18 Drawing Sheets

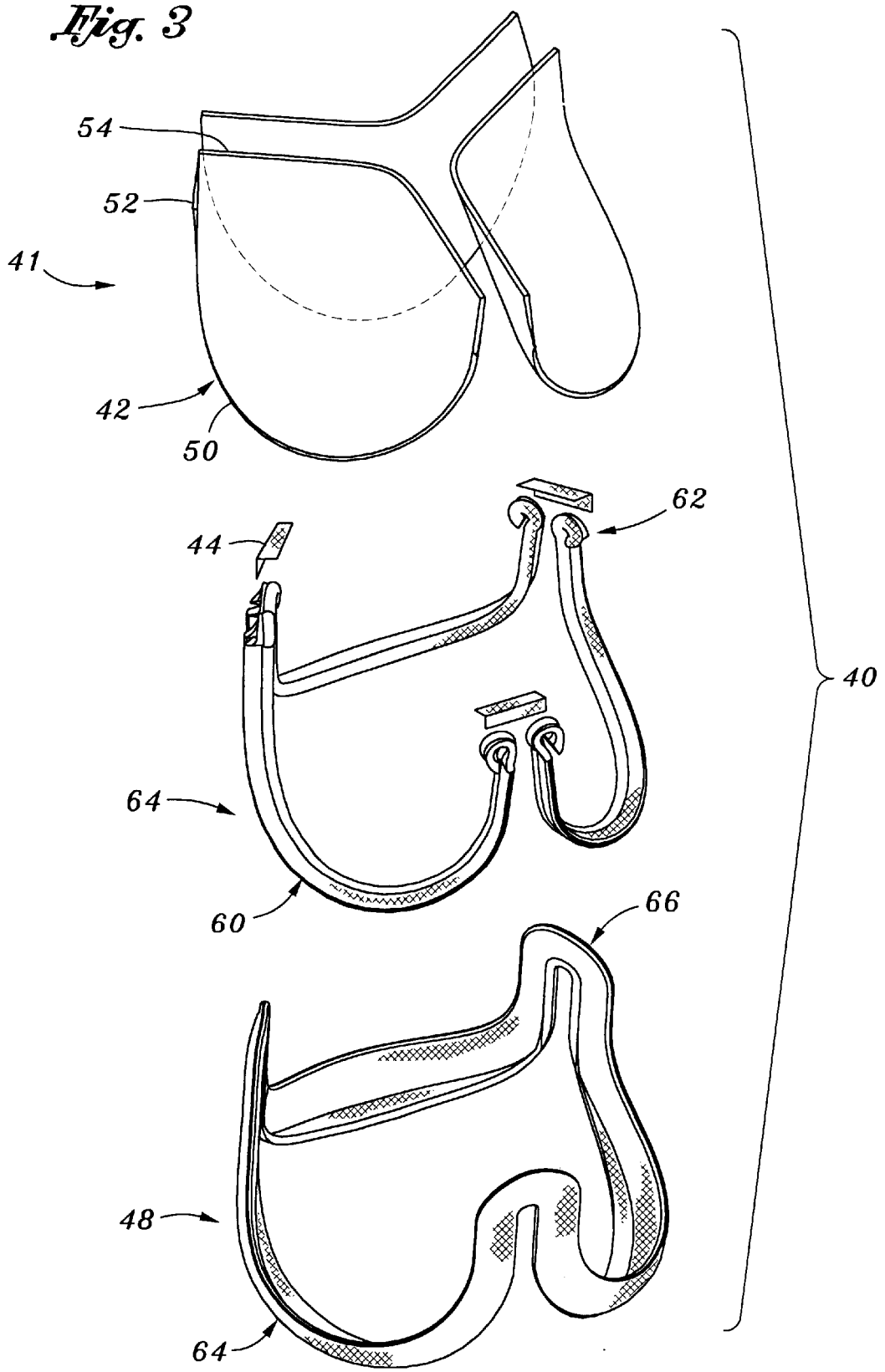

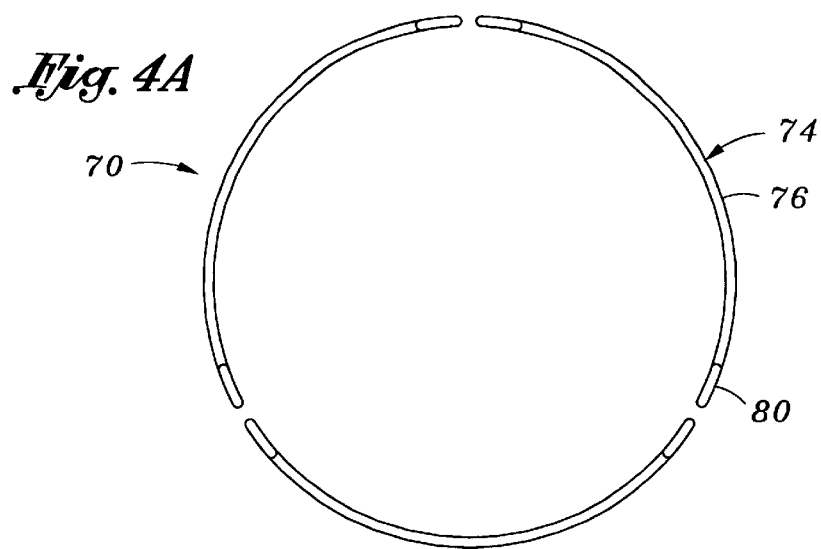
_Fig. 4A_
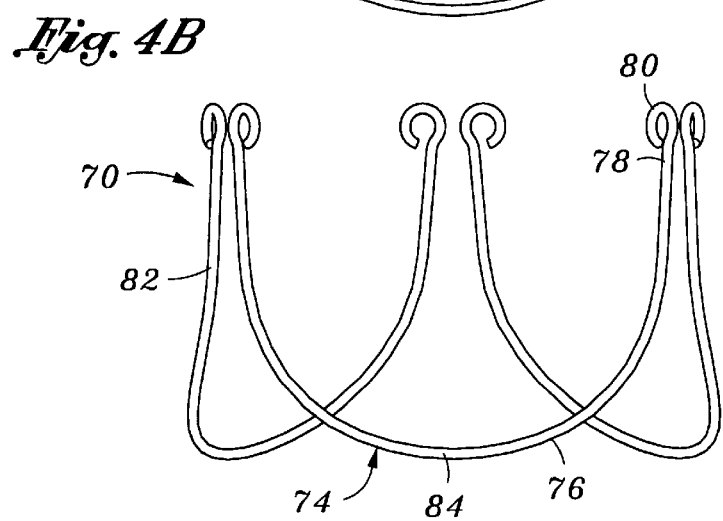
_Fig. 4B_
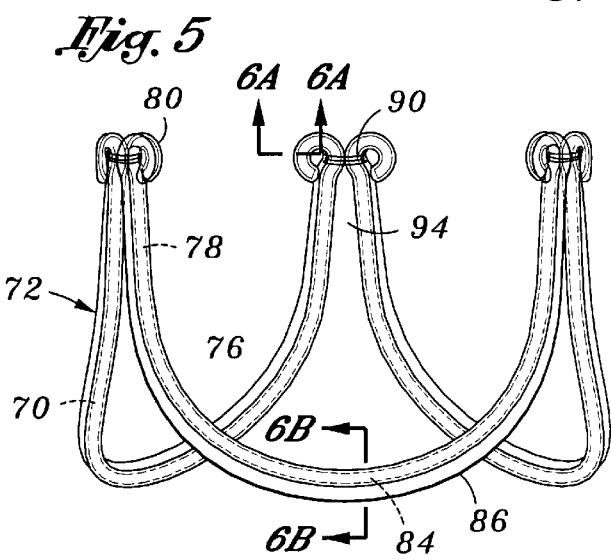
_Fig. 5_
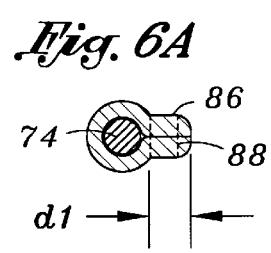
_Fig. 6A_
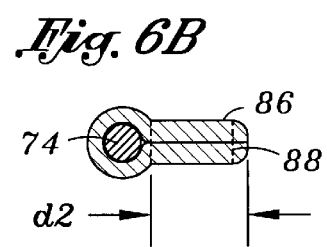
_Fig. 6B_

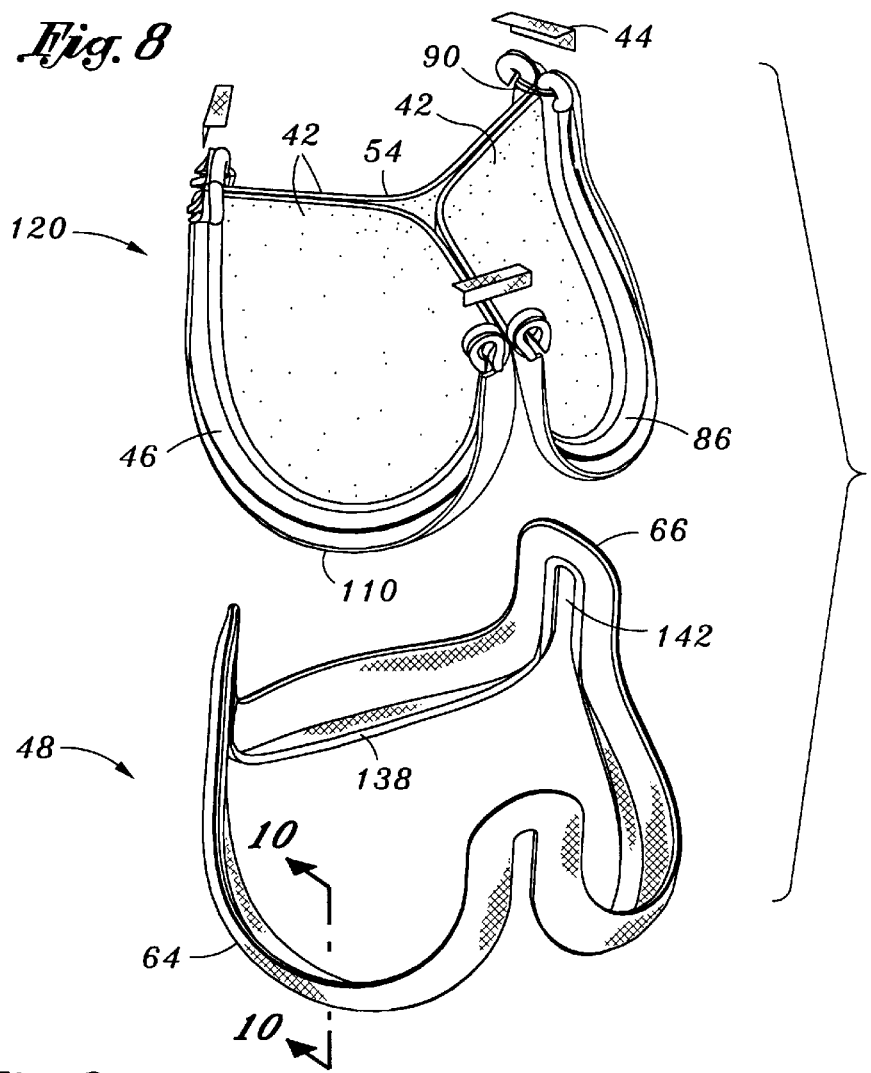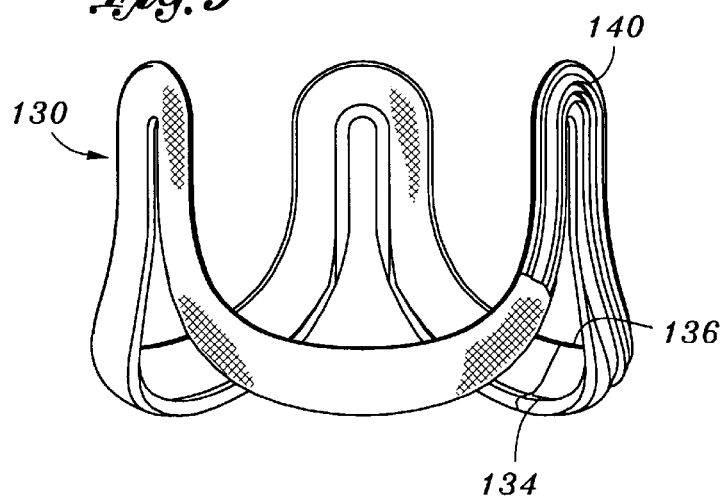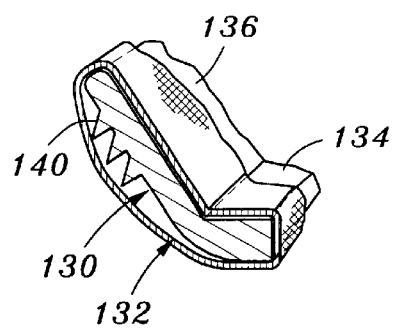

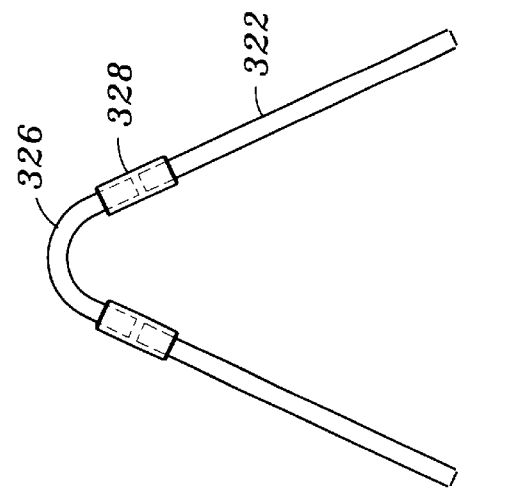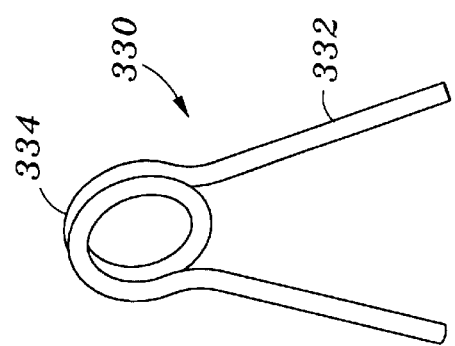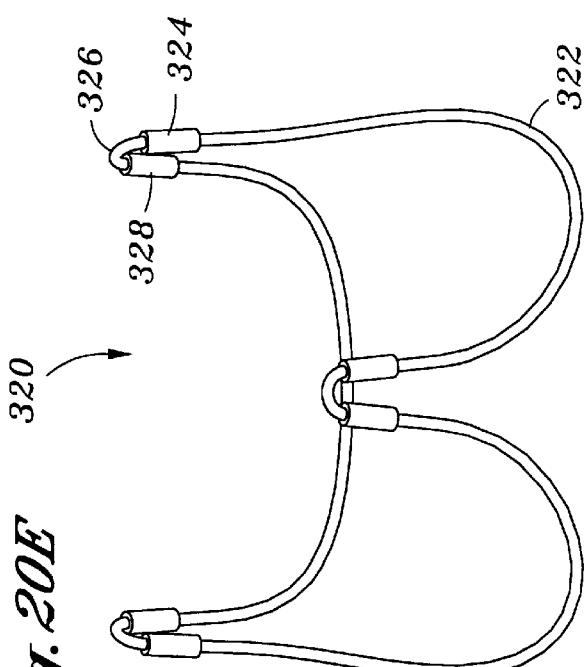

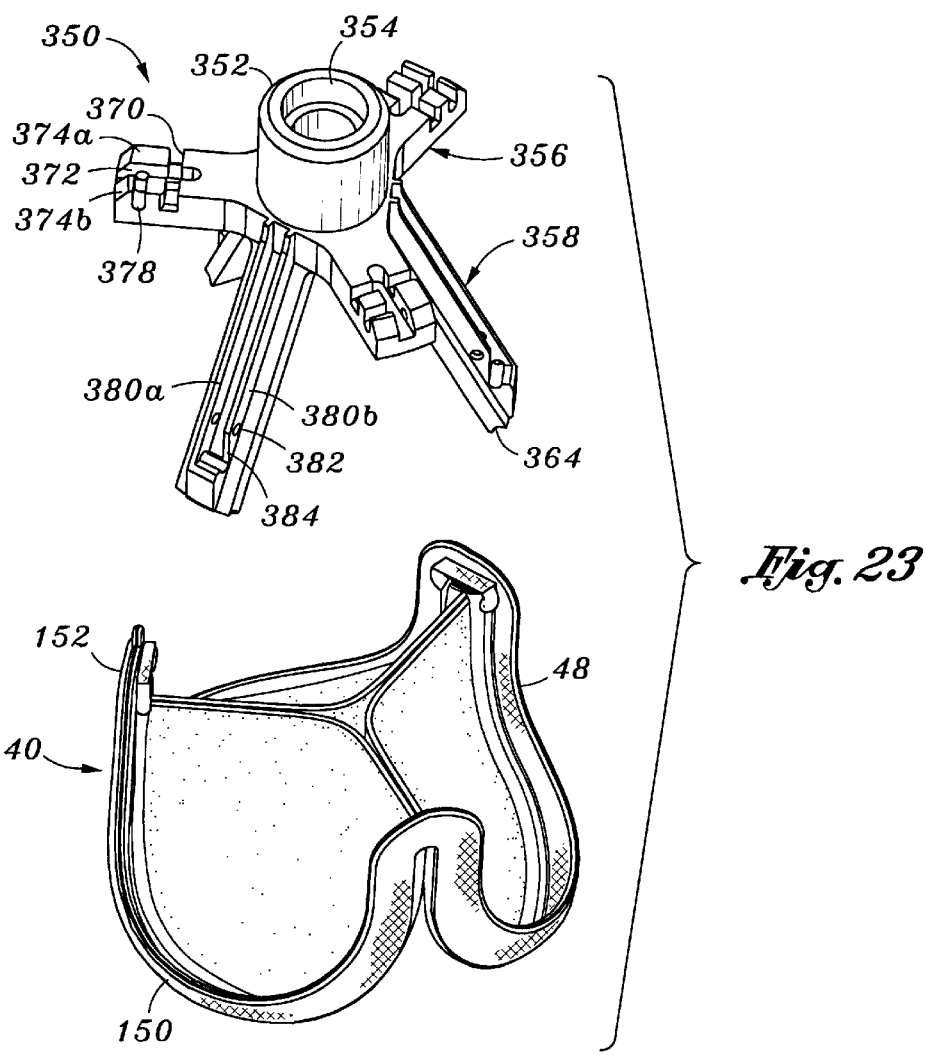
_Fig. 23_
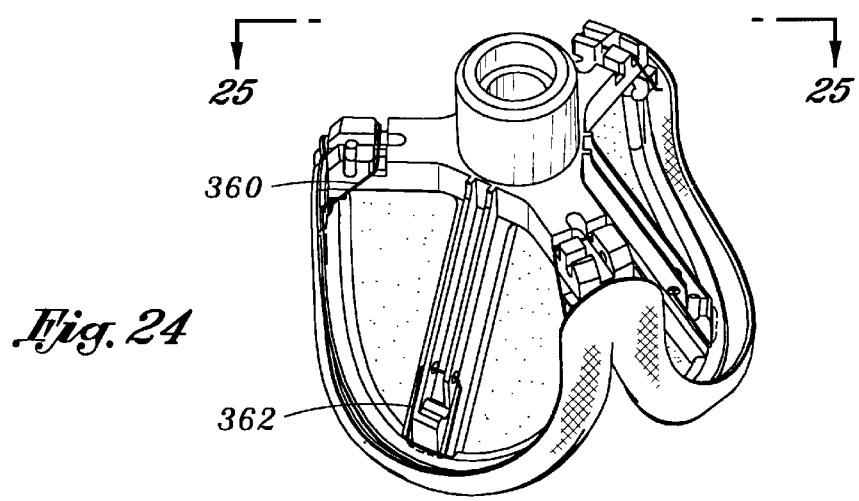
_Fig. 24_

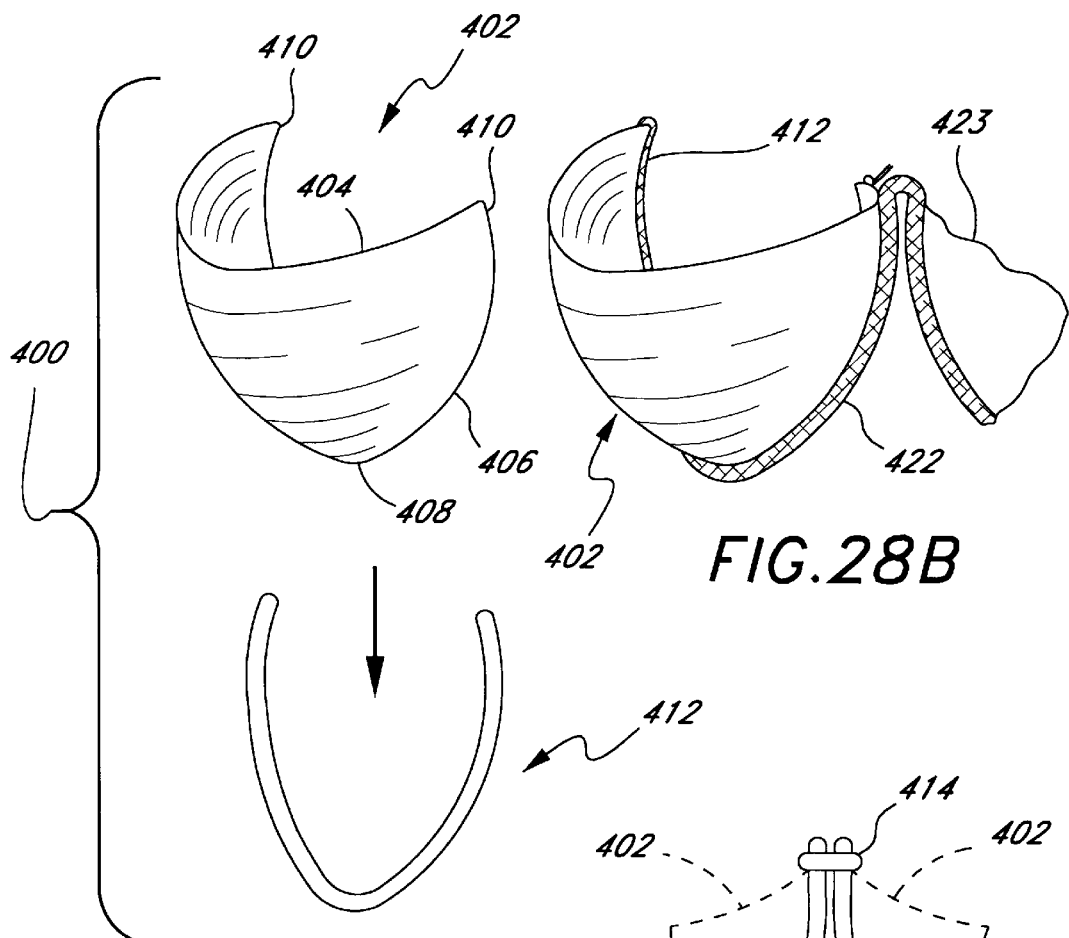
FIG.28A
FIG.28B
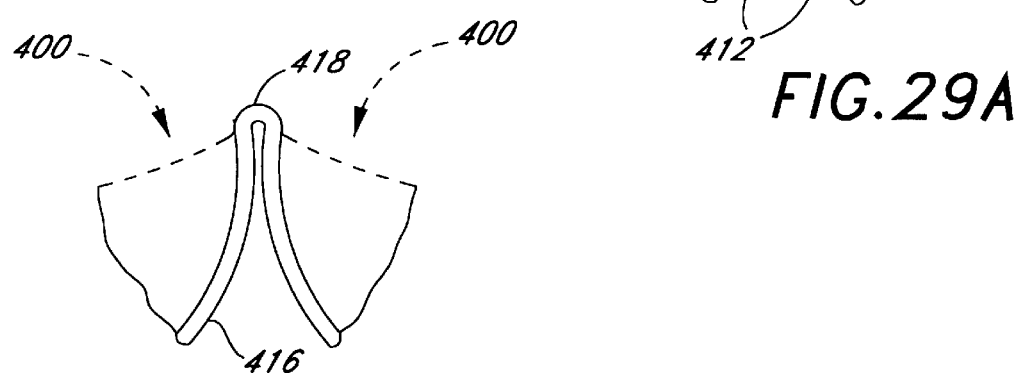
FIG.29A
FIG.29B

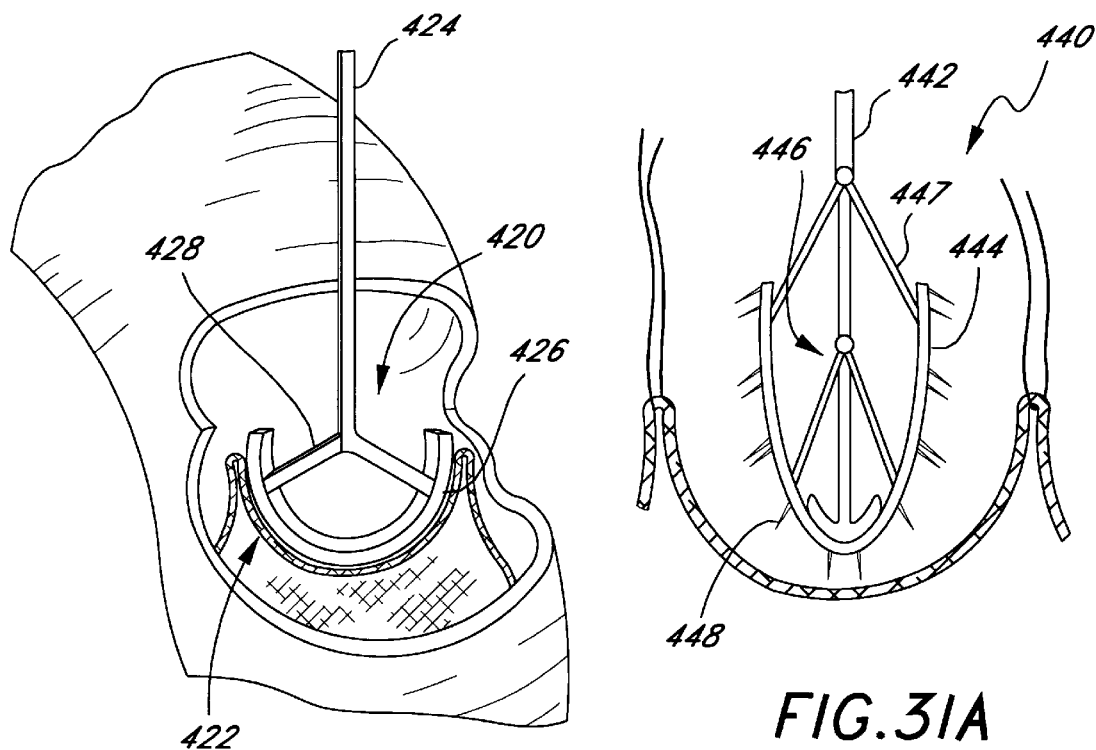
FIG. 30
FIG. 31A
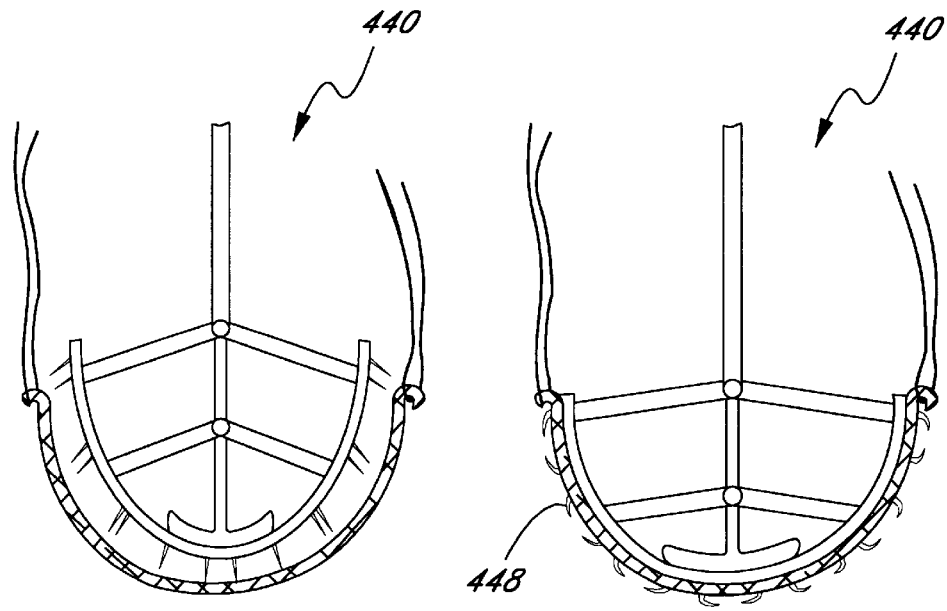
FIG. 31B
FIG. 31C

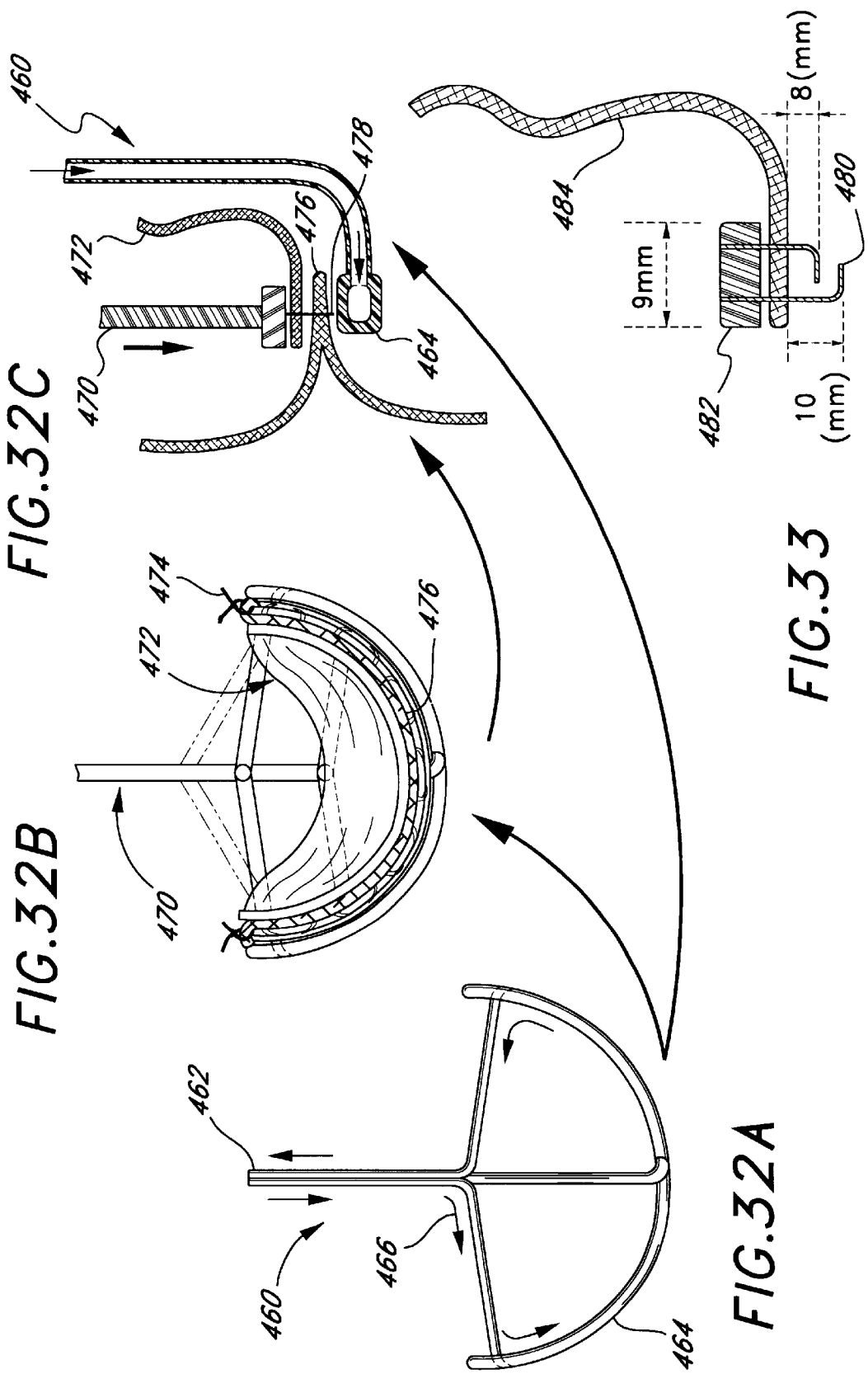

FLEXIBLE HEART VALVE LEAFLETS

RELATED APPLICATIONS

The present application is a continuation-in-part of U.S. application Ser. No. 09/332,759, filed Jun. 14, 1999, which claims priority from Provisional Application No. 60/117,445, filed Jan. 26, 1999, both having the same title.

FIELD OF THE INVENTION

The present invention relates to prosthetic heart valves, and, more particularly, to a prosthetic tissue valve having increased flexibility enabling it to follow the motions of the annulus and sinus regions.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way outflow valve. The natural heart valves are identified as the aortic, mitral (or bicuspid), tricuspid and pulmonary valves. The valves of the heart separate chambers therein, and are each mounted in an annulus therebetween. The annuluses comprise dense fibrous rings attached either directly or indirectly to the atrial and ventricular muscle fibers. Prosthetic heart valves can be used to replace any of these naturally occurring valves, although repair or replacement of the aortic or mitral valves are most common because they reside in the left side of the heart where pressures are the greatest. In a valve replacement operation, the damaged leaflets are excised and the annulus sculpted to receive a replacement valve.

The four valves separate each ventricle from its associated atrium, or from the ascending aorta (left ventricle) or pulmonary artery (right ventricle). After the valve excision, the annulus generally comprises a ledge extending into and defining the orifice between the respective chambers. Prosthetic valves may attach on the upstream or downstream sides of the annulus ledge, but outside of the ventricles to avoid interfering with the large contractions therein. Thus, for example, in the left ventricle a prosthetic valve is positioned on the inflow side of the mitral valve annulus (in the left atrium), or on the outflow side of the aortic valve annulus (in the ascending aorta).

Two primary types of heart valve replacements or prostheses are known. One is a mechanical-type heart valve that uses a ball and cage arrangement or a pivoting mechanical closure to provide unidirectional blood flow. The other is a tissue-type or "bioprosthetic" valve which is constructed with natural-tissue valve leaflets which function much like a natural human heart valve, imitating the natural action of the flexible heart valve leaflets which seal against each other to ensure the one-way blood flow.

Prosthetic tissue valves comprise a stent having a rigid, annular ring portion and a plurality of upstanding commissures to which an intact xenograft valve or separate leaflets of, for example, bovine pericardium are attached. The entire stent structure is typically cloth-covered and a sewing ring is provided around the periphery for attaching to the natural annulus. Because of the rigidity of the material used in the stent and/or wireform, conventional valves have a diameter that is minimally affected by the natural motion of the heart orifice. In the aortic position, the commissures extend in the downstream direction a spaced distance from the walls of the downstream aortic wall. Movement of the aortic wall or sinuses does not directly affect movement of the cantilevered commissures, though fluid flow and pressures generated by movement of the walls ultimately does cause the commissures to dynamically flex to some extent (i.e., they are cantilevered downstream in the aorta). Because of the inherent rigidity in conventional heart valves, the natural dilatation of the annulus is restricted, imposing an artificial narrowing of the orifice, and increasing the pressure drop therethrough.

Accordingly, there is a need for a more flexible heart valve that responds to the natural motions of the annulus and downstream vessel walls.

SUMMARY OF THE INVENTION

The present invention allows the prosthesis to follow the aortic wall motion as well as that of the annulus during systole and diastole phases, thus reducing the loss in pressure caused by restriction of such motions. The solution is a heart valve having a plurality of leaflets, preferably three, directly sutured to the aortic wall, replacing the native valve.

The present invention provides a heart valve including a flexible wireform or stent that allows relative cusp movement or pivoting. The continuous maintenance of leaflet orientation at the commissures provides durability and predictability. Though the leaflets are not wholly independent, they are allowed to move in regions of greatest anatomical motion.

The present invention differs in another respect from bioprosthetic tissue valves of the prior art because it does not include a conventional sewing ring with attendant rigid stent. Alternating peripheral cusps and commissures of the prosthetic valve are attached to the annulus region and the sinus region of the ascending aorta of the host (in the aortic valve version), downstream from the location of the natural leaflets (typically excised).

In accordance with one aspect of the present invention, a prosthetic heart valve is provided including a flexible, generally cylindrical stent having alternating cusps and commissures. A plurality of flexible leaflets is attached to the stent so as to form a one-way valve within the cylinder. A flexible band is attached along the stent and has a free edge extending away from the stent along the alternating cusps and commissures for connecting the heart valve to an anatomical orifice.

Another aspect of the present invention is a highly flexible heart valve including a stent/leaflet subassembly having a peripheral stent and a plurality of leaflets disposed therewithin. The stent/leaflet subassembly defines alternating cusps and the commissures. A connecting band is attached to the stent/leaflet subassembly and follows the alternating cusps and commissures. The band includes a free edge extending from the stent for connecting the heart valve to an anatomical orifice.

In a still further aspect of present invention, a prosthetic heart valve comprises a plurality of flexible leaflets, each having an arcuate cusp edge and a coapting edge. The heart valve includes a stent with a plurality of cusps connected to each other at upstanding commissures to generally define a substantially cylindrical volume therebetween. The leaflets are attached to the stent within the cylindrical volume and the cusps are free to move with respect to one another about the commissures.

In another embodiment, the present invention provides a prosthetic heart valve comprising a stent having a plurality of stent members adjacently disposed generally around a circle to define a substantially cylindrical volume therebetween. The stent includes a plurality of alternating cusps and commissures. Preferably, the stent members each have a cusp and two commissure regions, with adjacent commissure regions of the stent members together defining each of the commissures of the stent. The stent members may be coupled together to pivot or flexibly move with respect to one another. The coupling may be permanent, or may comprise a bio-resorbable structure that permits the stent members and associated leaflets to move independently from one another.

A further aspect of the invention is a heart valve having three leaflets which are directly sutured to the aortic wall, replacing the native valve. In one embodiment, the commissures of adjacent cusps may be connected during implant, and can become independent thereafter. This gives the cusps and commissures freedom to move during systole and diastole, thus improving the pressure gradient. To facilitate implantation, the commissures may be initially temporarily connected, such as with a biodegradable material. In a minimally invasive contexts, the valve may be partially collapsible to facilitate delivery through a narrow channel to the implantation site.

Alternatively, the invention provides a reduced pressure gradient prosthetic heart valve that has multiple, preferably three, totally or partially independent leaflets. The leaflets are directly sutured to the aortic wall, replacing the native valve. The commissures of adjacent leaflets may be connected during implant and become independent thereafter, or they may be linked together at the commissure. For example, adjacent commissures may be linked by fasteners that are either unique to each leaflet (a commissure clip or a clip in conjunction with a cusp support), or comprise a continuous scalloped wire or frame around all of the leaflets. The fastener must be sufficiently flexible to preserve the motion of the three leaflets during systole. Because of the independent (or flexibly coupled) nature of the leaflets, the commissures are free to move during the systole/diastole cycle, and the pressure gradient through the valve is therefore significantly reduced.

Still further, the invention contemplates the replacement of a single leaflet with an independent prosthetic leaflet, while the other native leaflets remain and are still functional. That is, if one native leaflet is not functioning because of disease or other condition, the entire valve need not be replaced, just the damaged leaflet. The present invention thus enables a less invasive procedure that obviates the removal of healthy leaflets. Still further, a minimally-invasive implantation device may be used to deliver and implant the independent leaflet(s).

Desirably, the stent of the prosthetic heart valve of the present invention is configured to permit the cusps and commissures to move radially in and out. In one embodiment, the stent comprises a cloth covered rod-like structure. The cloth covering closely surrounds the stent and includes a flap projecting therefrom substantially the entire length of the cusps and commissures for connecting the stent to both the flexible band and the leaflets. The band preferably comprises a suture-permeable inner member, such as silicone, covered by cloth. The cusps of the stent may be pivotally or flexibly coupled to each other at the commissures. Preferably, the stent comprises separate cloth-covered stent members that each define a cusp region and two commissure regions, adjacent commissure regions of the stent members together defining each of the commissures of the stent. The commissure regions of the separate stent members desirably remain spaced apart, with the leaflets extending therethrough to be attached between the cloth covering and the outer connecting band. In this manner, the leaflets are connected to separate stent members, and not to each other to facilitate flexing of the valve.

In another aspect of the present invention, a holder is provided for mounting the flexible heart valve. The holder includes a central hub with a plurality of radially outward upper legs, and a plurality of lower legs angled downward and outward. The upper and lower legs are adapted to connect to the alternating cusps and commissures of a flexible valve so as to maintain the position of the valve during implantation.

The present invention further provides a combination of a flexible prosthetic heart valve and a rigid holder. The flexible heart valve includes alternating cusps and commissures in a generally cylindrical configuration adapted to move radially in and out with respect to one another. The holder includes structure for maintaining a fixed shape of the flexible prosthetic heart valve during implantation.

In a still further aspect of the present invention, a heart valve leaflet is provided comprising a flexible, planar body having an arcuate cusp edge terminating at outer tips. The planar body includes a coapting edge that is defined by two relatively angled lines joined at an apex directed away from the cusp edge midway between the two tips. Desirably, the leaflet is made of pericardial tissue.

The present invention further provides a method of implantation of a heart valve, including the steps of: providing a flexible heart valve having alternating cusps and commissures in a generally cylindrical configuration and adapted to move radially in out with respect to one another; attaching a holder to the valve that restricts relative movement of the cusps and commissures; positioning the heart valve in proximity to an anatomical orifice; implanting the heart valve; and, disconnecting the holder from heart valve.

BRIEF DESCRIPTION OF THE DRAWINGS

FIG. 3 is an exploded perspective view illustrating subassemblies of a prosthetic heart valve of the present invention;

FIG. 4A is a top plan view of an internal stent of the prosthetic heart valve of the present invention;

FIG. 4B is an elevational view of the internal stent of FIG. 4A;

FIG. 5 is an elevational view of a stent assembly of the prosthetic heart valve;

FIGS. 6A and 6B are sectional views through two locations of the stent assembly, taken along lines 6A—6A and 6B—6B of FIG. 5;

FIG. 8 is an exploded perspective view of a stent/leaflet sub-assembly and a connecting band of the prosthetic heart valve of the present invention;

FIG. 9 is an elevational view of an inner member of the connecting band;

FIG. 10 is a cross-sectional view through a cusp of the connecting band shown in FIG. 8;

FIGS. 20A–20E are elevational views of alternative stents for use in a prosthetic heart valve in accordance with the present invention;

FIG. 21 is a detailed view of a commissure region of the alternative stent of FIG. 20E;

FIG. 22 is a detailed view of a commissure region of a still further alternative stent accordance with the present invention;

FIG. 23 is an exploded perspective view of the prosthetic heart valve of the present invention and a holder used during implantation of the valve;

FIG. 24 is a perspective view of the holder coupled to the valve;

FIG. 28A is a perspective exploded view of an independent leaflet for use with other such leaflets that are attached directly to an ascending aorta and function together as a prosthetic valve;

FIG. 28B is a perspective assembled view of the independent leaflet of FIG. 28A;

FIG. 29A is an elevational view of one embodiment of an attachment structure between two of the adjacent independent leaflets of FIG. 28B;

FIG. 29B is an elevational view of a continuous structure for attaching the independent leaflets of FIG. 28B;

FIG. 30 is a perspective view of an exemplary device for measuring the native tissue prior to select the appropriate sized independent leaflet of FIG. 28B for implantation;

FIGS. 31A–31C are schematic views of a device for automatically implanting an independent leaflet of the present invention, illustrating a collapsible articulated holder especially suited for minimally invasive environments;

FIGS. 32A–32C are schematic views of a further device for automatically implanting an independent leaflet of the present invention, illustrating a multi-part holder for installing attachment staples; and FIG. 33 is a cross-sectional view through one embodiment of an attachment structure for the independent leaflet embodiment, or for multi-leaflet embodiments for that matter.

DESCRIPTION OF THE PREFERRED EMBODIMENTS

The present invention provides a highly flexible aortic heart valve that is attached generally along a scalloped or undulating perimeter downstream from where the natural leaflets were originally attached. The natural leaflets include arcuate cusp portions separated by common commissure portions. If the natural valve has three leaflets, and has a vertically oriented flow axis, the leaflets are evenly distributed circumferentially 120° apart with lower cusp portions and upstanding commissure portions. The commissure portions are connected between the cusp portions and are generally axially aligned along the aortic wall. The annular root of an aortic valve is composed of fibrous tissue and generally conforms to the undulating perimeter of the valve to support the leaflets. In this respect, implanting the aortic heart valve of the present invention involves excising the natural leaflets and attaching the prosthetic heart valve proximate the fibrous annulus, but also in part up the aortic wall. Because of the particular construction of the present heart valve, as will be described below, the attachment means, be it sutures, staples, adhesives, or otherwise, may be anchored into the aortic wall itself, adjacent to the fibrous annulus.

Anatomy

Figure 2:
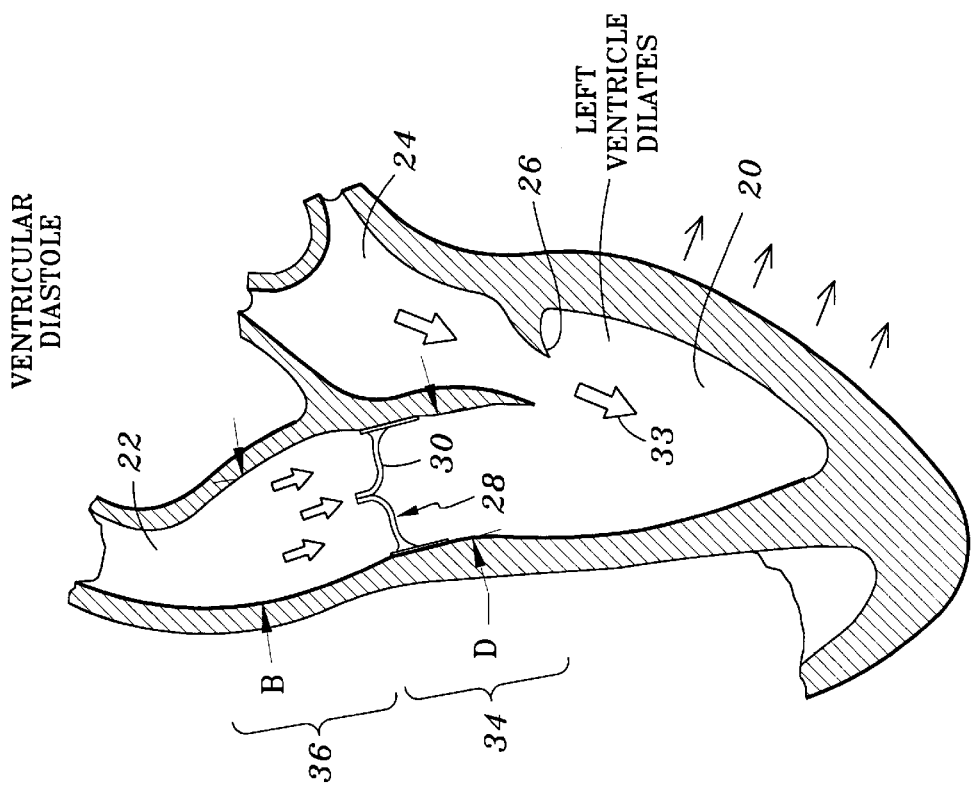
FIG. 2 is a sectional view through the left half of a human heart showing a diastolic phase of left ventricular expansion.
Figure 1:
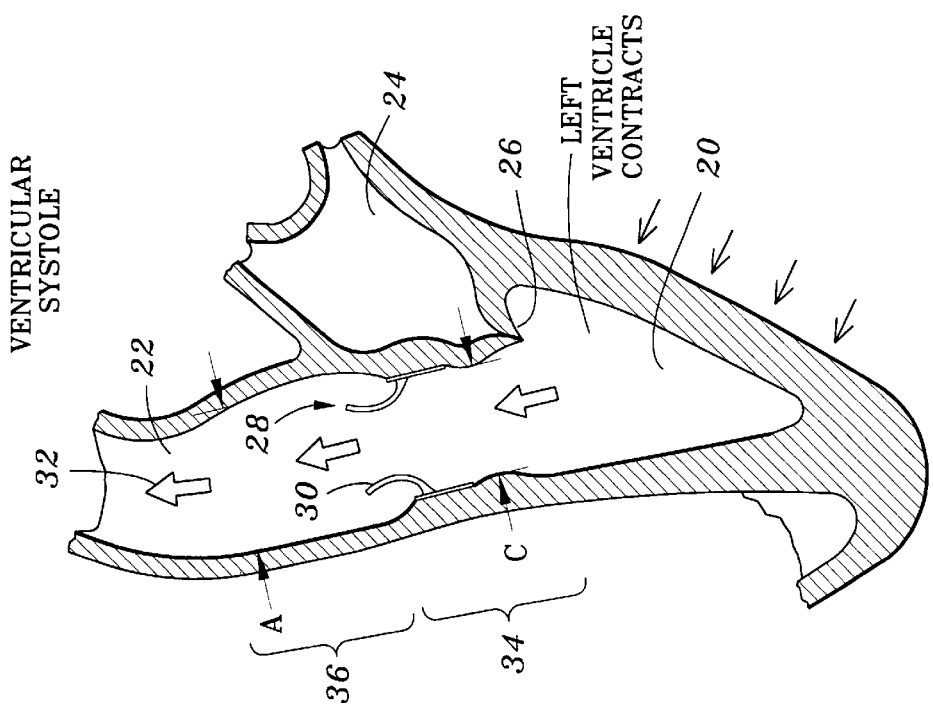
FIG. 1 is a sectional view through the left half of a human heart showing a systolic phase of left ventricular contraction.

To better illustrate the advantages of the flexible heart valve of the present invention, an understanding of the movement of the annulus and aorta is helpful. In this regard, FIGS. 1 and 2 illustrate the two phases of left ventricular function; systole and diastole. Systole refers to the pumping phase of the left ventricle, while diastole refers to the resting or filling phase. FIGS. 1 and 2 illustrate in cross section the left chamber of the heart with the left ventricle 20 at the bottom, and the ascending aorta 22 and left atrium 24 diverging upward from the ventricle to the left and right, respectively. FIG. 1 illustrates systole with the left ventricle 20 contracting, while FIG. 2 illustrates diastole with the left ventricle dilating. The aortic valve 28 is schematically illustrated here as having leaflets 30. Contraction of the ventricle 20 causes the mitral valve 26 to close and the aortic valve 28 to open, and ejects blood through the ascending aorta 22 to the body's circulatory system, as indicated in FIG. 1 by the arrows 32. Dilation of the ventricle 20 causes the aortic valves 28 to close and mitral valve 26 to open, and draws blood into the ventricle from the left atrium 24, as indicated in FIG. 2 by the arrows 33.

The walls of the left chamber of the heart around the aortic valve can be generally termed the annulus region 34 and the sinus region 36. The annulus region 34 generally defines an orifice that is the narrowest portion between the ventricle 20 and ascending aorta 22, which as noted above is composed of generally fibrous tissue. The sinus region 36 is that area just downstream from the annulus region 34 and includes somewhat elastic, less fibrous tissue. Specifically, the sinus region 36 typically includes three identifiable, generally concave sinuses (formally known as Sinuses of Valsalva) in the aortic wall intermediate the upstanding commissures of the valve 28. The sinuses are relatively elastic and are constrained by the intermediate, more fibrous commissures of the aortic annulus. Those of skill in the art will understand that the annulus region 34 and sinus region 36 are not discretely separated into either fibrous or elastic tissue, as the fibrous commissures of the annulus extend into the sinus region 36.

The sinuses tend to move in and out to facilitate fluid dynamics of the blood in conjunction with systole and diastole. During systole, as seen in FIG. 1, the sinus region 36 expands somewhat to a diameter A. This facilitates blood flow through the ascending aorta 22 to the rest of the body. In contrast, during the diastolic phase as seen in FIG. 2, the sinus region 36 contracts somewhat to a smaller diameter B. The diameters A and B are intended to be a measurement of the radial movement of the commissure regions of the valve 28. In this regard it will be understood that the cross-sections shown are not taken in a single plane, but instead are taken along two planes angled apart 120° with respect one another and meeting at the midpoint of the aorta 22. The sinus region 36 has a neutral, or relaxed diameter (not shown) somewhere in between diameters A and B.

The annular region 34 also moves in and out during the systolic and diastolic phases. As seen in FIG. 1, the annular region 34 contracts somewhat to a diameter C during systole. In contrast, during the diastolic phase as seen in FIG. 2, the annular region 34 expands somewhat to a larger diameter D. Much like the sinus region 36, the annular region 34 has a neutral, or relaxed diameter (not shown) somewhere in between diameters C and D.

As will be explained more fully below, the prosthetic valve of the present invention accommodates the in and out movements of both the annular region 34 and the sinus region 36. That is, alternating peripheral portions of the prosthetic valve are attached to the annular region 34 and the sinus region 36 and move accordingly. It is important to point out that the preceding discussion of dynamic movement of the annulus and sinus regions is based on preliminary understanding of such movement. That is, direct measurements of these movements are problematic, and thus certain assumptions and predictions must be made. The actual dynamic movement in any particular human heart may be different, but the principles of the present invention would still apply. That is, relative movement in the annulus and sinus regions during systole and diastole does exist, and the flexible prosthetic heart valve of the present invention can accommodate any such movement.

Valve Subassemblies

Figure 11:
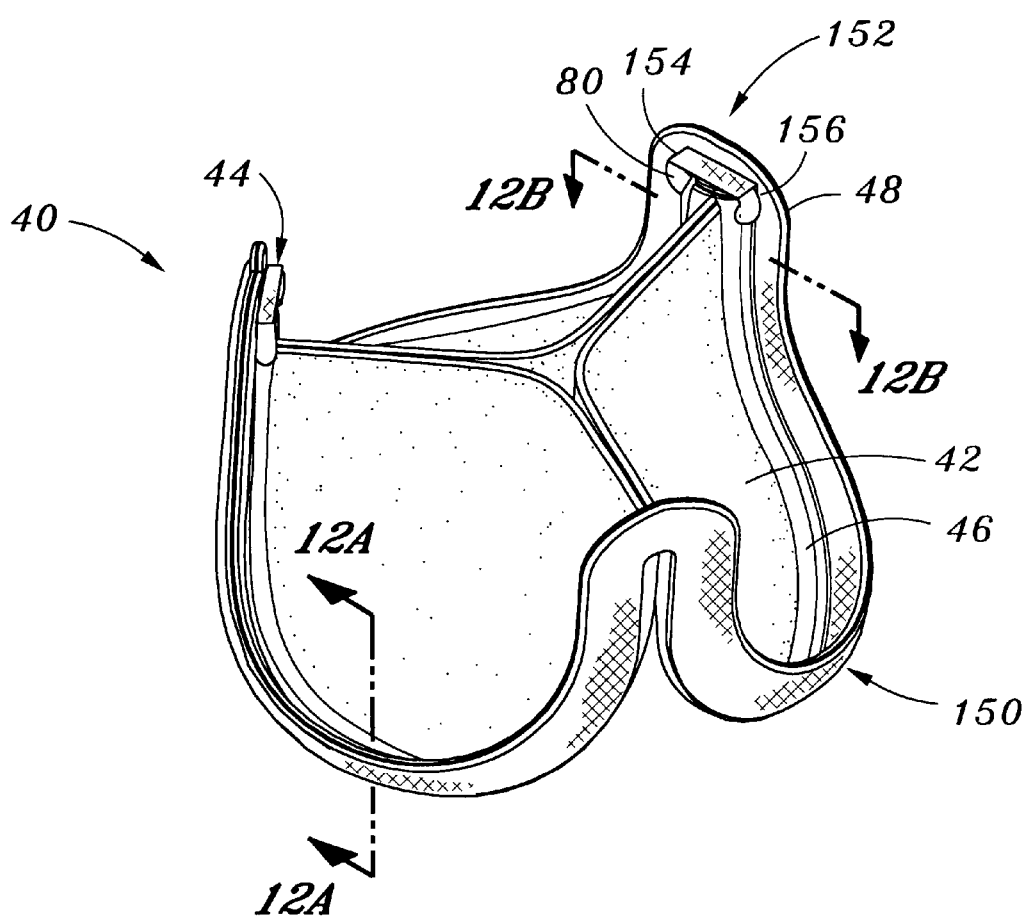
FIG. 11 is a perspective view of an assembled prosthetic heart valve of the present invention.

With reference now to FIG. 3, the primary sub-assemblies of a preferred embodiment of the prosthetic heart valve 40 of the present invention are shown in exploded view. For purposes of discussion, the directions up and down, upper and lower, or top and bottom, are used with reference to FIG. 3, but of course the valve can be oriented in any direction both prior to and after implantation. From top to bottom, the heart valve 40 comprises a group 41 of three leaflets 42, three angled alignment brackets 44, a stent assembly 46, and a connecting band 48. Each of the sub-assemblies seen in FIG. 3 is procured and assembled separately (except for the group of leaflets, as will be explained), and then joined with the other sub-assemblies to form the fully assembled valve 40 as seen in FIG. 11.

The prosthetic valve 40 is a trifoliate valve with three leaflets 42. Although three leaflets are preferred, and mimic the natural aortic valve, the principles of the present invention can be applied to the construction of a prosthetic valve with two or more leaflets, depending on the need.

Each of the sub-assemblies seen in FIG. 3 include three cusps separated by three commissures. The leaflets 42 each include an arcuate lower cusp edge 50 terminating in upstanding commissure regions 52. Each leaflet 42 includes a coapting or free edge 54 opposite the cusp edge 50. In the assembled valve 40, the cusp edges 50 and commissure regions 52 are secured around the periphery of the valve, with the free edges 54 permitted to meet or "coapt" in the middle. The stent assembly 46 also includes three cusps 60 separated by three upstanding commissures 62. In like manner, the connecting band 48 includes three cusp portions 64 separated by three upstanding commissure portions 66. Each of the sub-assemblies will now be described in detail.

Stent Assembly

Various components of a preferred stent assembly 46 are seen in FIGS. 4–6. The stent assembly 46 comprises an inner stent 70 and an outer cloth cover 72. More specifically, the inner stent 70 desirably includes three identical and separate stent members 74, each of which has a separate cloth covering. As seen best in FIG. 4B, each stent member 74 comprises an arcuate lower cusp region 76 and upstanding commissure regions 78 each terminating at a tip 80. The stent members 74 comprise elongate rods or wires, preferably made out of an elastic biocompatible metal and/or plastic alloy, such as Elgiloy®, Nitinol, polypropylene, etc.. The material selected for stent members 74 should be elastic to permit flexing along their lengths, but should possess a relatively high modulus of elasticity to avoid asymmetric deformation of the constructed valve 40. The stent 70 supplies an inner frame for the valve 40 that is relatively more rigid than the other components. Therefore, the stent 70 acts to limit total flexibility of the valve 40.

The stent members 74 are desirably bent into the illustrated shape, using conventional wire-forming techniques. Each of the stent members 74 is identical, and terminates in the tips 80 which are bent inward with respect to the arcuate cusp regions 76 to nearly form closed circles. As is seen in FIG. 4B, a gradual radially outward bend 82 (with respect to the cylindrical stent 70) is provided in the stent members 74 at a transition between each of the commissure regions 78 and the intermediate cusp region 76. This bend 82 permits each of the stent members 74 to remain in a circular configuration, as seen from above in FIG. 4A. That is, if the cusp regions 76 extended in a plane between each of the commissure regions 78, the plan view would be somewhat triangular. Instead, each of the cusp regions 76 includes a lower apex 84, and the apices of all of the cusps define a circle concentric with and having the same diameter as a circle defined by all of the tips 80. The stent 70 thus defines a substantially cylindrical volume therewithin. Of course, other volumes may be defined by the stent 70 wherein the tips 80 define a circle that is smaller or larger than a circle defined by the apices 84. For example, the apices 84 may be provided outward from the tips 80 so the stent 70 defines a frusto-conical volume therewithin.

As seen in FIG. 5, each of the stent members 74 is preferably covered with a generally tubular cloth 72 from tip to tip 80. The cloth cover 72 is a biocompatible fabric, such as polyterephthalate, and has a varying cross sectional shape, as indicated in FIGS. 6A and 6B. More specifically, the cloth cover 72 includes a tubular portion closely conforming around each of the stent members 74 and a flap 86 extending radially outward from the stent member (with respect to the curvature of the cusp regions 76). The cloth cover 72 is formed by wrapping an elongated sheet of fabric around each of the stent members 74 and joining the free edges with sutures 88 to form the flaps 86. As seen in FIG. 5, the flap 86 extends from each stent member 74 in a direction that is generally outward with respect to the cusp region 76, and continues in the same general orientation up the commissure regions 78 to the tips 80. The flap 86 has a dimension that is longest at the apex 84 of each cusp region 76 and shortest at the tips 80. Indeed, the flap 86 is preferably nonexistent at the tips 80, and gradually increases in size from the tip 80 to the apex 84. Therefore, the cross-section of FIG. 6A taken through the commissure region 78 shows the flap 86 having a small dimension d1, and the cross-section of FIG. 6B taken through the apex 84 shows the flap 86 having a longer dimension d2.

The final component of the stent assembly 46 is an attachment means 90 for joining each of a cloth-covered stent members 74. Preferably, the attachment means 90 comprises threads or sutures sewn through the central holes in each of the circular tips 80, as shown in FIG. 5, although other suitable attachment means could be used, such as rings, cinches, or the like. The attachment means 90 may be wrapped around or sewn through the cloth cover 72. In joining the tips 80, the attachment means 90 are desirably not wrapped extremely tightly, but are instead provided with some slack to permit relative movement of the tips, as will be described below. When the stent members 74 are attached, as seen in FIG. 5, the stent 70 exhibits three cusps corresponding to the cusp region 76 of each member, and three upstanding commissures defined by the juxtaposition of adjacent pairs of commissure regions 78.

In a preferred embodiment of the present invention the attachment means 90 comprises a non-bioresorbable material to ensure that the individual stent members 74 are maintained in the shape of the stent 70. In an alternative configuration, however, the attachment means 90 comprises a bioresorbable material that dissolves over a period of time after implantation. In such an embodiment, the natural host tissues may have grown in and around the porous portions of the valve 40 to help retain the original shape of the stent 70. In some instance, however, very little tissue overgrowth may have occurred prior to the attachment means 90 dissolving, and the individual stent members 74 are permitted to move radially a great deal with respect to one another. In the latter embodiment, wherein the stent members 74 are permitted to spread apart, the connecting band 48 may be re-configured to be non-continuous at the commissure portions 66 (see FIG. 3). As a consequence, each individual stent member 74 and associated leaflet 72 moves entirely independently of the others, albeit all oscillating with the natural contractions and expansions of the surrounding aortic wall. Such independent leaflet movement may greatly reduce any potential pressure drop across the valve. Although one embodiment is to provide a bioresorbable attachment means 90 such as the sutures shown in the embodiment of FIG. 5, those of skill in the art will understand that any of the coupling means connecting the individual stent members 74 disclosed in the present application could be modified to resorb over time.

The stent assembly 46 provides an inner support frame that is generally rigid along any one of stent members 74, but which permits the stent members to move with respect to one another. In this context, "generally rigid" refers to the structural strength of the stent members 74 that is sufficient to maintain the general shape of the stent 70, but that permits some flexing along the length of the stent members. Though the stent members 74 are generally rigid, they are able to move with respect to one another. More particularly, joining the stent members 74 with the attachment means 90 creates nodes or pivot points of the valve 40 at the commissures 62 of the stent assembly 46. As will be more fully explained below with reference to FIGS. 13–16, the stent members 74 are permitted to pivot with respect to one another as they move radially inward and outward. Inward pivoting is permitted by spaces 94, seen in FIG. 5, defined between adjacent cloth-covered commissure regions 78 of each stent member 74. These regions 94 are generally triangular and gradually increase in size from the attached commissure tips to the diverging cusps.

Leaflet Configurations

Figure 7A:
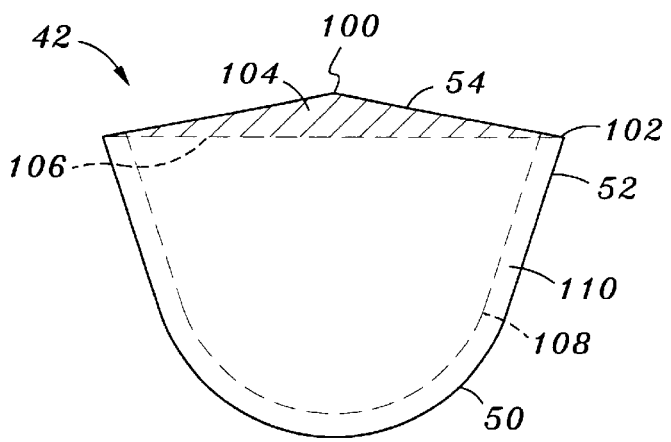
FIGS. 7A, 7B, and 7C are plan views of leaflets suitable for use in the prosthetic heart valve of the present invention.
Figure 7B:
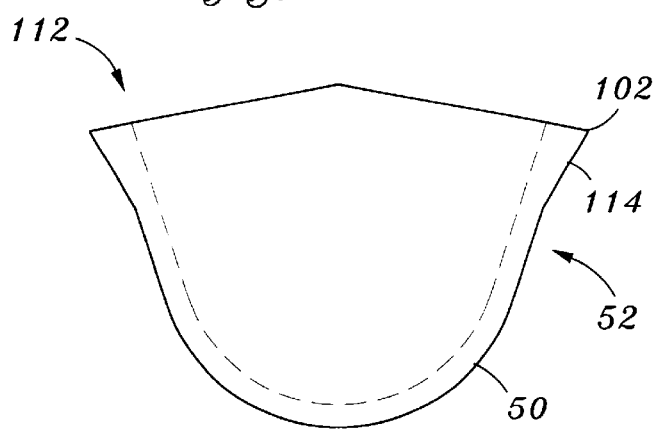
Figure 7C:
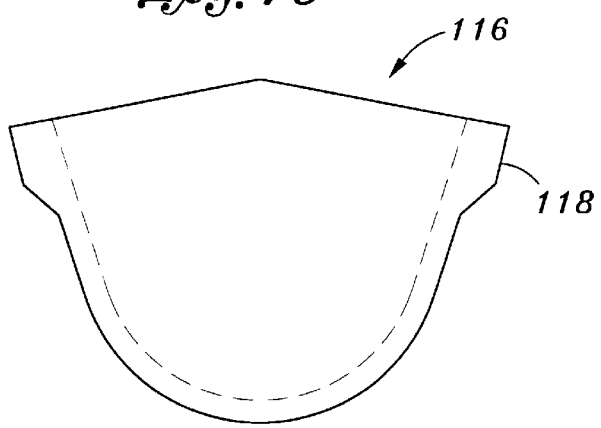

FIGS. 7A, 7B, and 7C are plan views of various configurations of leaflets 42 suitable for use in the prosthetic heart valve 40. FIG. 7A shows a leaflet 42 having the aforementioned cusp 50, commissure regions 52, and free edge 54. It will be noted that the coapting edge 54 comprises two linear portions extending from an apex 100 to outer tips 102. The two portions of the free edge 54 are angled with respect to one another and define sides of a triangular region 104 having as its hypotenuse an imaginary line 106 extending between the opposed tips 102. The triangular region 104 of each leaflet 42 is under less tension during dynamic motion of the valve 40, and helps ensure coaptation of the leaflets. That is, the leaflets 42 are generally secured along the cusp 50 and commissure regions 52, and thus the majority of each leaflet 42 is placed in stress except in the region above imaginary line 106. In this regard, an imaginary (dashed) fold line 108 defines an outer margin 110 of the leaflet 42 that is used to secure the leaflets into the valve 40. As will be clear from the discussion below, the margins 110 are sutured between the stent assembly 46 and connecting band 48 (FIG. 3), and the free edge 54 of the leaflet extends across the cylindrical region defined within the valve 40, and is generally free to move in that region. Because the triangular leaflet region 104 is relatively stress-free, it tends to roll over under the influence of fluid dynamic forces, thus helping the three leaflets to coapt and prevent valve insufficiency.

FIG. 7B shows a leaflet 112 that is substantially the same as the leaflet 42 of FIG. 7A, and thus like elements will be given the same numbers. The leaflet 112 includes a pair of generally triangular shaped commissure tabs 114 in the commissure regions 52. The tips 102 are thus spaced farther apart than in the version shown in FIG. 7A. The commissure tabs 114 are used to more securely fasten each of the leaflets to the commissures 62 of the stent assembly 46 (FIG. 3). The cloth cover 72 of the stent assembly 46 includes a flap 86 (FIG. 5) which diminishes in size in the commissure regions. The tabs 114 are thus wrapped farther around the cloth-covered stent assembly 46 in the commissure regions and sutured thereto, thus facilitating a more durable connection.

FIG. 7C is a further variation of a leaflet 116 which is, again, the same in all respects to the leaflets described above, except for somewhat trapezoidal-shaped commissure tabs 118. Again, the commissure tabs 118 help to secure the leaflets 116 in the prosthetic valve 40.

Stent/Leaflet Sub-Assembly

FIG. 8 illustrates a stent/leaflet sub-assembly 120 in which the leaflets 42 are secured to the stent assembly 46. Preferably, leaflets 42 are pre-attached to align the free edges 54. In this manner, the free edges 54 of each two adjacent leaflets 42 extend outward in juxtaposition and are received within the triangular space 94 defined between the commissure regions 78 of the stent assembly 46 (FIG. 5). The group of leaflets 41 is thus "inserted" underneath the stent assembly 46 until the juxtaposed free edges 54 of the leaflets 42 are in close proximity below the attachment means 90. The outer margin 110 of each leaflet 42 is folded underneath the corresponding cusp 60 of the stent assembly 46. At this point, sutures or other such means attach the margins 110 to the flap 86 of the stent assembly 46. The leaflets 42 can remain attached to one another at their adjacent tips 102 (or along the free edges 54 near the tips), or can be separated for maximum valve flexibility or when the stent is designed to separate into individual stent members by bio-resorption of a commissure couple.

If either the leaflet 112 or leaflet 116 of FIG. 7B or 7C are used, the respective commissure tabs 114 or 118 are wrapped around the adjacent part of the stent assembly 46 and secured thereto. In a preferred assembly method, the leaflets 42 are simply retained in position with respect to the stent assembly 46 with temporary sutures or other such means, to permit the stent/leaflet subassembly 120 to be finally joined together with the connecting band 48 of FIG. 8.

FIG. 8 also illustrates the three alignment brackets 44 and that each has a generally L-shaped cross-section and comprises a cloth-covered inner member (not separately numbered). The inner member preferably has minimum elasticity, but is relatively thin and lightweight. One preferred material for the inner member is a polyester film such as Mylar®. The brackets 44 are preferably joined to the valve 40 at the time the stent/leaflet sub-assembly 120 and connecting band 48 are joined, and thus will be described more fully below with respect to FIG. 11.

Connecting Band

FIGS. 9 and 10 illustrate the connecting band 48 in more detail, comprising an inner member 130 surrounded by a cloth cover 132. As mentioned previously with respect to FIG. 3, the connecting band 48 includes three cusp portions 64 alternating with commissure portions 66, all generally formed in a tubular configuration. This shape is provided by the inner member 130, with the cloth cover 132 simply draped and sewn thereover. In a preferred embodiment, the inner member 130 is molded of silicone rubber, and the cloth cover 132 is polyterephthalate.

The inner member 130 has a varying cross sectional shape along the cusps and commissures. FIG. 10 is cross-section through one of the cusp portions 64 of the connecting band 48, and shows a region of the inner member 130 having an inner ledge 134 and upwardly angled outer free margin 136. The cloth-covered ledges 134 extend generally radially and define three stent support regions 138 of the connecting band 48, as seen in FIG. 8. The ledge 134 has its greatest radial dimension at the midpoint of each of the cusp portions 64 and gradually tapers down in size toward the commissure portions 66. Likewise, the free margins 136 form their greatest outward angle with respect to a central axis of the connecting band 48 at each cusp portion 64, and gradually re-align to be parallel to the central axis in the commissure portions 66. The cross-section of the inner member 130 at the commissure portions 66 is seen in FIG. 12B. A series of triangular shaped ribs 140 projects outward from the inner member 130. The ribs 140 are formed around the entire inner member 130, along both the cusp and commissure regions. As seen in FIG. 8, the commissure portions 66 of the connecting band 48 define generally axial gaps 142 that help permit flexing of the valve 40. It should be noted that the connecting band 48 may be discontinuous at the commissure portions 66 if the valve has bioresorbable commissures and is designed to separate into individual "leaflets."

Assembled Valve

Figure 12A:
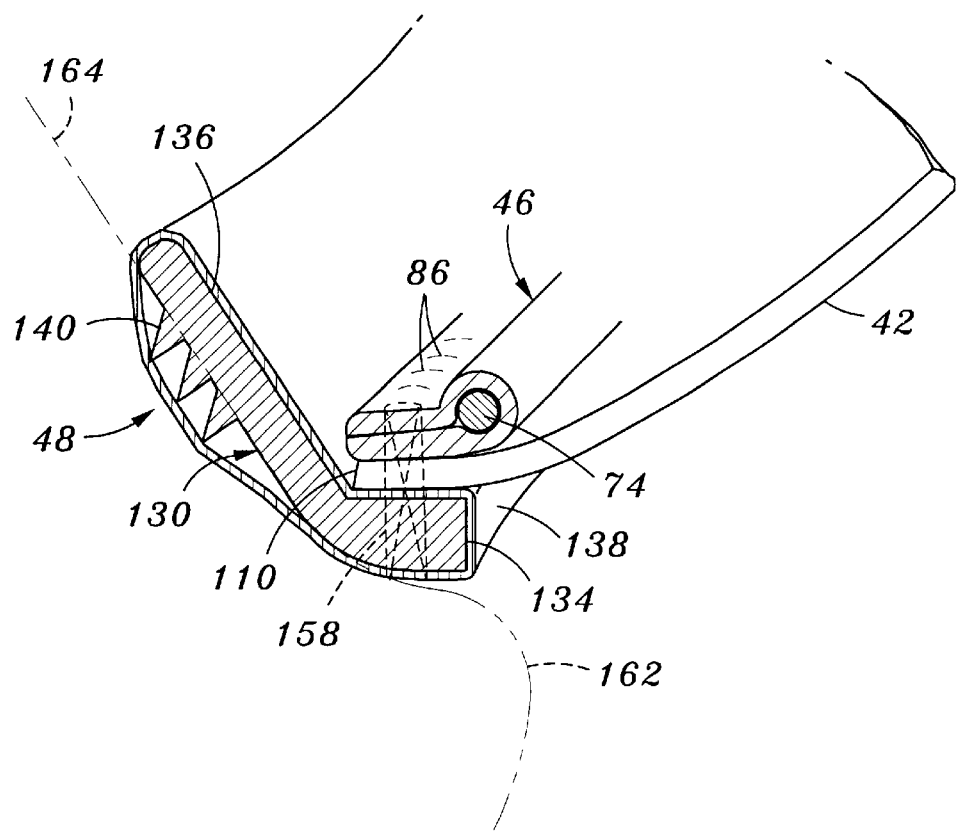
FIG. 12A is a cross-sectional view through a cusp region of the prosthetic heart valve of the present invention, taken along line 12A—12A of FIG. 11, and showing a portion of the host annulus in phantom.
Figure 12B:
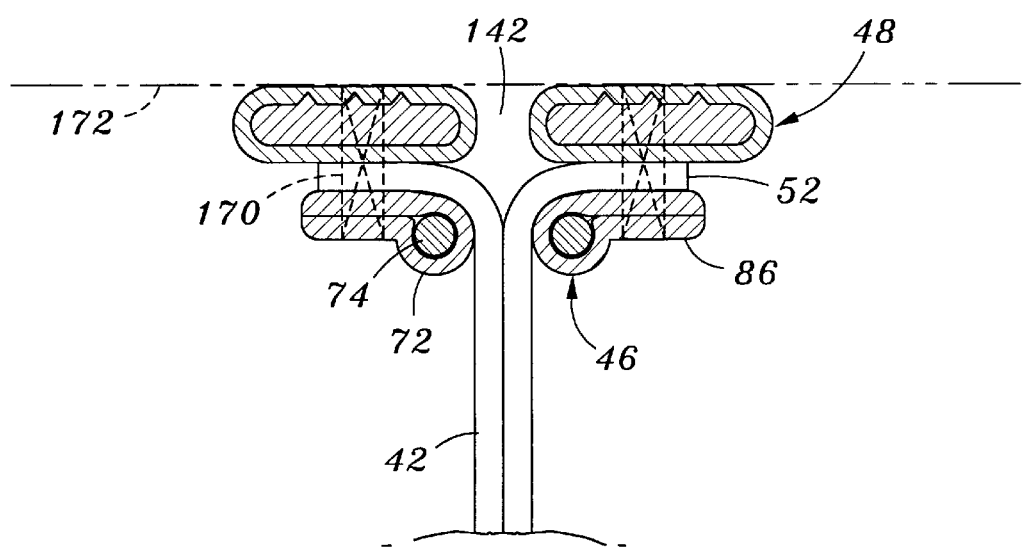
FIG. 12B is a cross-sectional view through a commissure region of the prosthetic heart valve of the present invention, taken along line 12B—12B of FIG. 11, and showing a portion of the host aortic wall in phantom.

FIG. 11 illustrates the assembled valve 40 in perspective, while FIGS. 12A and 12B show cross-sections through a valve cusp 150 and valve commissure 152, respectively. The connecting band 48 is sewn or otherwise attached to the exterior of the stent/leaflet subassembly 120. Actually, as seen in FIG. 12A, the connecting band 48 is attached underneath the stent/leaflet subassembly 120 in the cusp 150, but the free margins 136 of the connecting band are positioned to the outside of the subassembly. In addition, the alignment brackets 44 are installed with a vertical leg 156 interposed between the commissures 62 of the stent assembly 46 and the commissure portions 66 (FIG. 3) of the connecting band 48. A horizontal leg 154 of each of the alignment brackets 44 projects radially inward to cover the tips 80 of the stent assembly 46. The alignment brackets 44 help hold each two adjacent tips 80 of the three-piece stent 70 together, especially helping to prevent radial misalignment. The brackets also provide flat surfaces which a holder can contact, as seen best in FIG. 26.

With reference to the cross-section of FIG. 12A, the sandwiched configuration of the stent assembly 46, leaflet 42, and connecting band 48 can be seen. More specifically, the cloth flap 86 of the stent assembly 46 aligns with the leaflet margins 110, which in turn rest on the stent supports 138. A series of suture stitches 158 are used to secure these elements together. Preferably, the flap 86 terminates at the same location as the margin 110 of each leaflet 42, and at the corner defined in the connecting band 48 between each ledge 134 and free margin 136. The radially innermost wall of the ledge 134 is preferably inward from the stent member 74. This construction helps prevent the stent 70 from migrating downward with respect to the connecting band 48.

The host annulus 162 is seen in phantom with the aortic wall 164 continuing upward therefrom. It can be readily seen that the angled shape of the cusp portions 64 of the connecting band 48 conform nicely to the host annulus region. The triangular ribs 140 provide volume at the free margins 136 of the connecting band 48 to facilitate connection to the natural tissue; in other words, more volume provides more of a "bite" for the surgeon to secure the band 48 with a suture needle. Although the conventional means for attaching the valve 40 to the host tissue is with sutures, which are not shown, the present invention should not be construed as limited to being implanted with sutures and other means such as staples, adhesives, and the like could be used.

Now with reference to FIG. 12B, the assembly of the valve components in the commissure region is seen. The commissure edges 52 of each of the leaflets 42 are sandwiched in between the stent assembly 46 and connecting band 48. More particularly, the commissure edges 52 are sandwiched between the flaps 86 and the generally planar commissure portions 66 of the connecting band 48 (FIG. 8). Sutures 170 are provided to join these elements together. Again, the commissure edges 52 preferably terminate at the same location as the flaps 86. FIG. 12B also illustrates the gap 142 provided in the commissure regions of the connecting band 48, and the lack of structural connection between the two sides of each valve commissure 152.

FIG. 12B shows in phantom a portion of the aortic wall 172 to which the commissures 152 of the valve 40 are attached. Again, the particular attachment means is not shown, but the connecting band 48 is traditionally sutured to the wall 172.

Dynamic Motion of the Prosthetic Heart Valve

Figure 13:
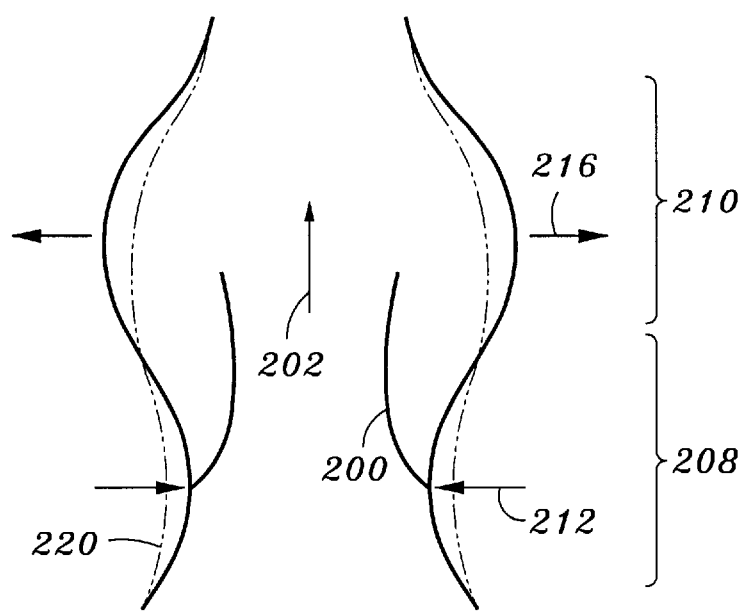
FIG. 13 is a schematic view showing relative movement of the aortic and annulus walls during systolic flow.
Figure 15:
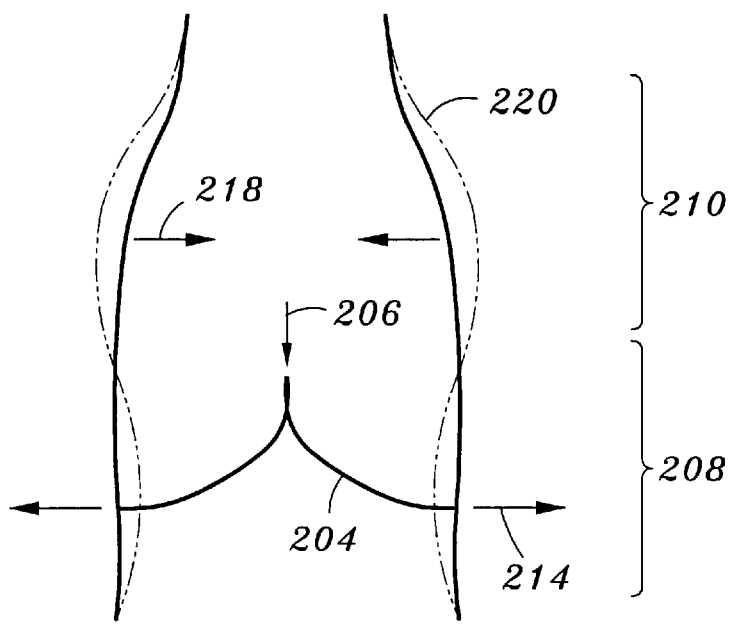
FIG. 15 is a schematic view showing relative movement of the aortic and annulus walls during diastolic flow.

FIGS. 13 and 15 illustrate a conduit portion of a heart in the region of the aortic valve and relative motions of the conduit walls during systole and diastole, respectively. In particular, FIG. 13 shows an open valve 200 and systolic blood flow 202, while FIG. 15 shows a closed valve 204 and diastolic back flow of blood 206. As described with respect to FIGS. 1 and 2, the regions around the aortic valve can be generally separated into an annulus region 208 and a sinus region 210.

As mentioned previously, the annulus region 208 is expected to contract during the systolic phase, as indicated by the arrows 212 in FIG. 13, and expand during the diastolic phase, as indicated by the arrows 214 in FIG. 15. Conversely, the sinus region 210 is expected to expand during the systolic phase, as indicated by the arrows 216 in FIG. 13, and is expected to contract during the diastolic phase, as indicated by the arrows 218 in FIG. 15. The movements of the conduit walls are shown with respect to a neutral or relaxed position 220, and may be exaggerated from the true movements. Also, as mentioned above, these movements are educated guesses and may be different for some, if not most patients. However, the flexible heart valve of the present invention accommodates all variations of such movements.

FIGS. 14 and 16 schematically illustrate the synchronous movement of the prosthetic valve 40 of the present invention with respect to the movements of the host tissue in systolic and diastolic phases as seen in FIGS. 13 and 15. To simplify this explanation, FIGS. 14 and 16 only illustrate the stent 70 of the present invention, which as previously described acts as a limitation to movement of the entire valve 40 and fairly represents movement of the entire valve.

Figure 14A:
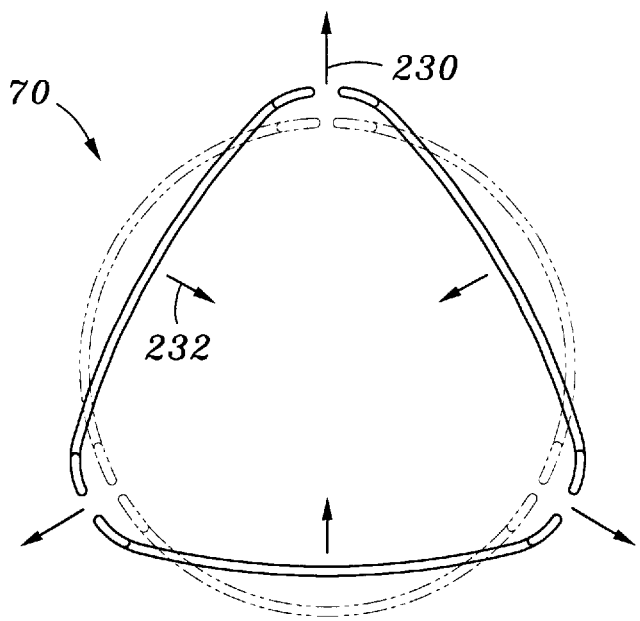
FIG. 14A is a plan view of only the stent members of the prosthetic valve flexed in accordance with the anatomical motions during systole shown in FIG. 13.
Figure 14B:
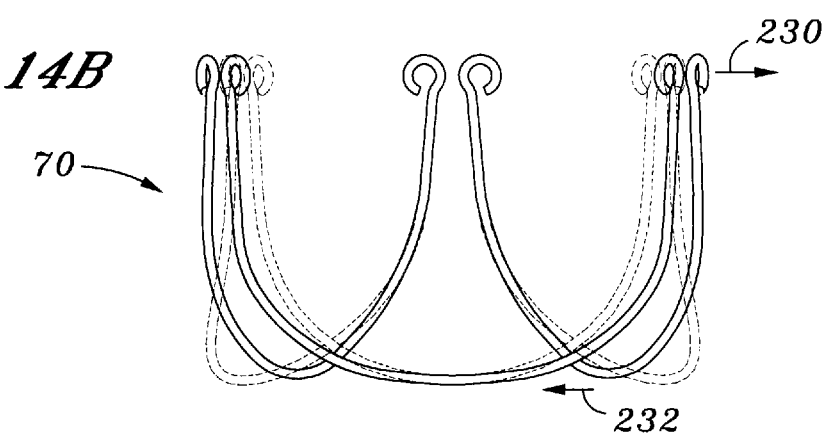
FIG. 14B is an elevational view of the stent members flexed in accordance with the anatomical motions during systole shown in FIG. 13.
Figure 16A:
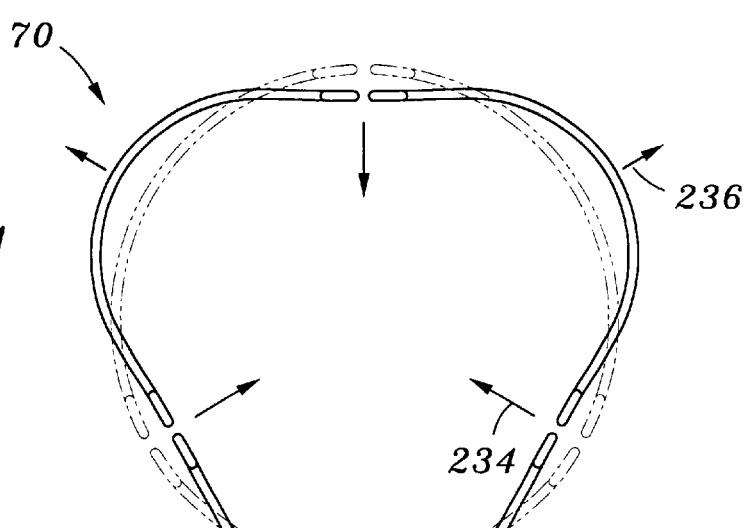
FIG. 16A is a plan view of only the stent members of the prosthetic valve flexed in accordance with the anatomical motions during diastole shown in FIG. 15.
Figure 16B:
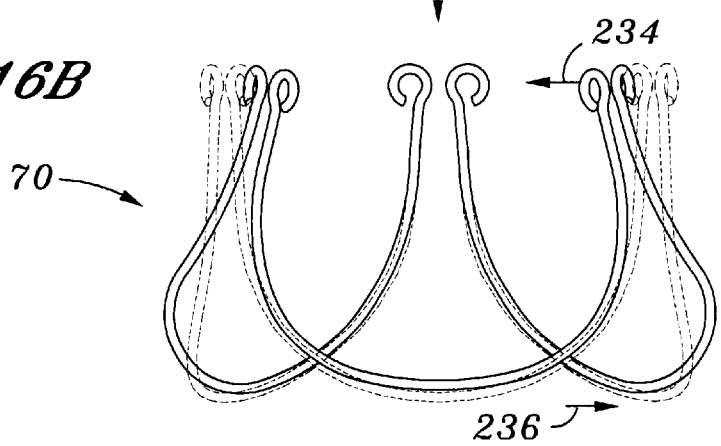
FIG. 16B is an elevational view of the stent members flexed in accordance with the anatomical motions during diastole shown in FIG. 15.

With reference to FIGS. 14A and 14B, during systole the valve experiences outward commissure movement, as indicated by the arrows 230. At the same time, the valve experiences inward movement at the cusps, as indicated by the arrows 232. During diastole, in contrast, and as seen in FIGS. 16A and 16B, the valve experiences inward commissure movement, as indicated by the arrows 234. At the same time, the valve experiences outward movement at the cusps, as indicated by the arrows 236.

Alternative Stents

Figure 17:
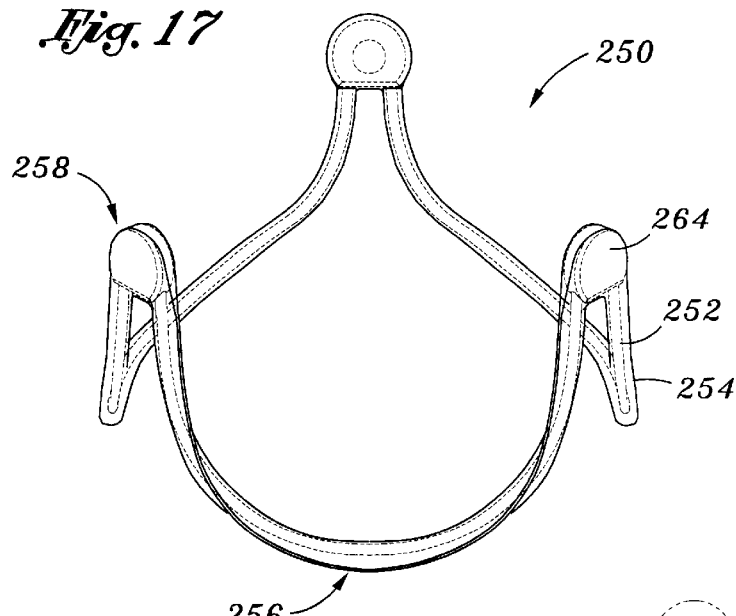
FIG. 17 is a perspective view of an alternative stent assembly for use in a prosthetic heart valve in accordance with the present invention.
Figure 18:
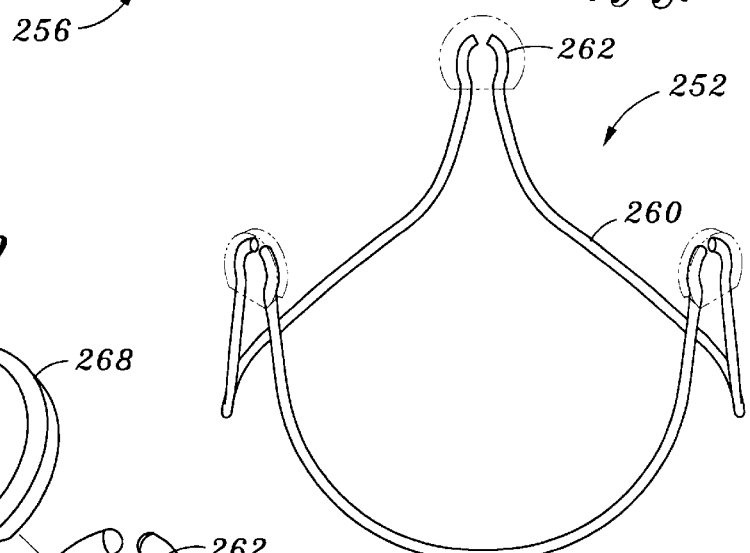
FIG. 18 is a perspective view of an internal stent of the stent assembly of FIG. 17.
Figure 19:
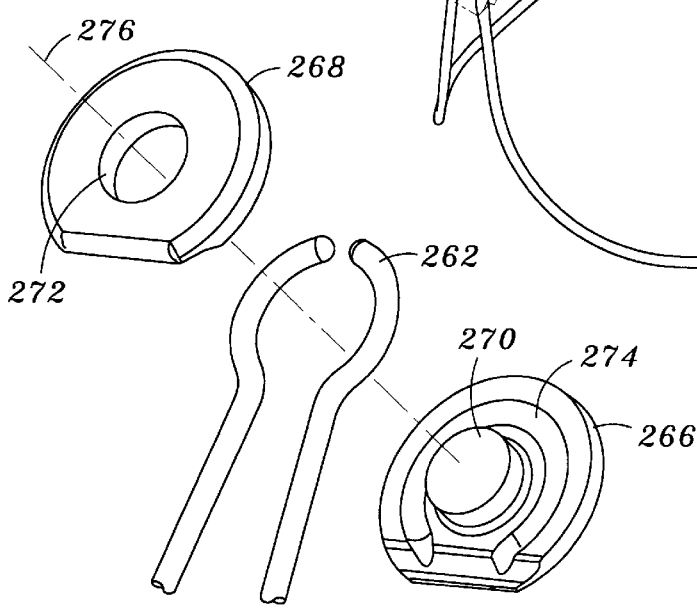
FIG. 19 is an exploded view of a commissure tip region of the stent assembly of FIG. 17.

FIGS. 17–19 illustrate an alternative stent assembly 250 comprising an inner stent 252 and an outer cloth cover 254. As with the earlier stent assembly 46, the stent assembly 250 includes alternating cusps 256 and commissures 258. As best seen in FIG. 18, the stent 252 includes three separate stent members 260 having arcuate commissure tips 262 that are curved toward one another. A generally disk-shaped commissure housing 264 encompasses the adjacent commissure tips 262, retaining the stent members 260 together while permitting relative pivoting.

FIG. 19 illustrates two adjacent commissure tips 262 and the commissure housing 264 exploded into a male housing portion 266 and a female housing portion 268. The housing portions are so named because they are joined together through interference between a button 270 of the male housing portion 266 and an aperture 272 on the female housing portion 268. Each portion of the commissure housing 264 includes a circular groove 274 for receiving the arcuate tips 262. The grooves 274 combined to form a circular channel having an axis 276 within which the arcuate tips 262 are received and can slide. When assembled together, the commissure housings 264 thus provide nodes of rotation for each of the stent members 260.

Figure 20A:
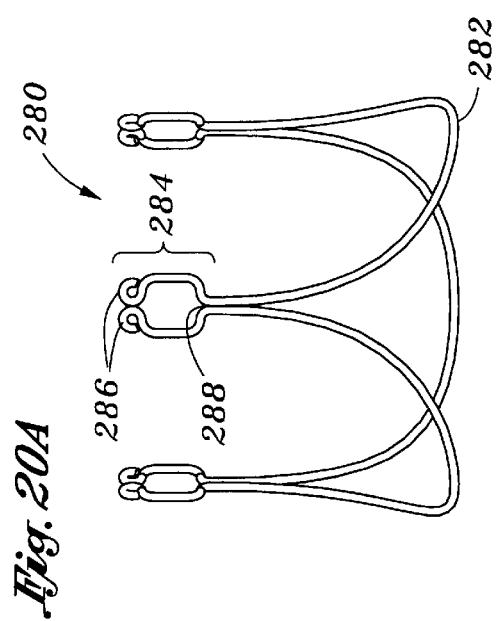

FIG. 20A illustrates an alternative stent 280 suitable for use in a heart valve of the present invention. The stent 280 includes three stent members 282, each having commissures with a flex region 284 and tips 286. The tips 286 of adjacent stent members 282 are secured together by sutures or other suitable means (not shown). The flex regions 284 comprise sections of each stent member 282 which are bent away from each other. The stent members 282 can thus pivot with respect to one another about the connected tips 286. Upon inward movement of the stent members 282, a fulcrum 288 is created by interaction between the stent members at the lower end of the flex region 284. The relative flexibility in inward or outward movement of the stent members 282 can be modified by selection of the cross sectional size and shape of the stent members, and overall configuration of the flex region 284.

Figure 20B:
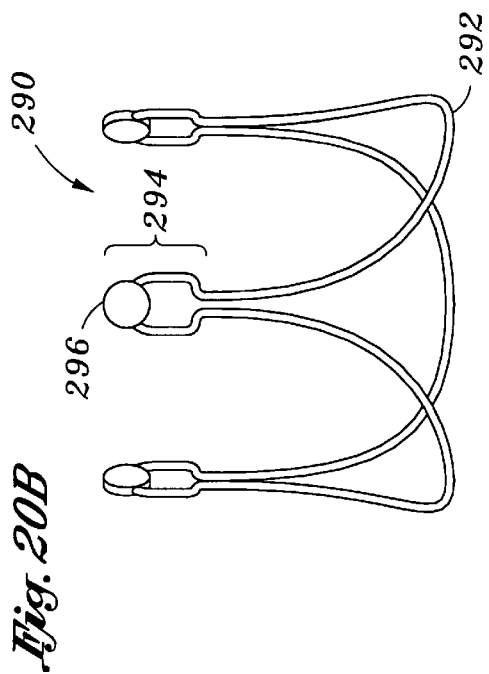

FIG. 20B illustrates a second alternative stent 290 suitable for use in a heart valve of the present invention. The stent 290 includes three wires 292 and has commissure regions 294 formed by bent ends of the wires and a junction member 296. In this embodiment, the junction member 296 either rigidly holds the terminal ends of each of the wires 292, or permits the wires to slide or otherwise flex with respect to one another. If the wires are rigidly attached to the junction member 296 the shape of the wires in the commissure region 294 reduces stress risers in bending.

Figure 20C:
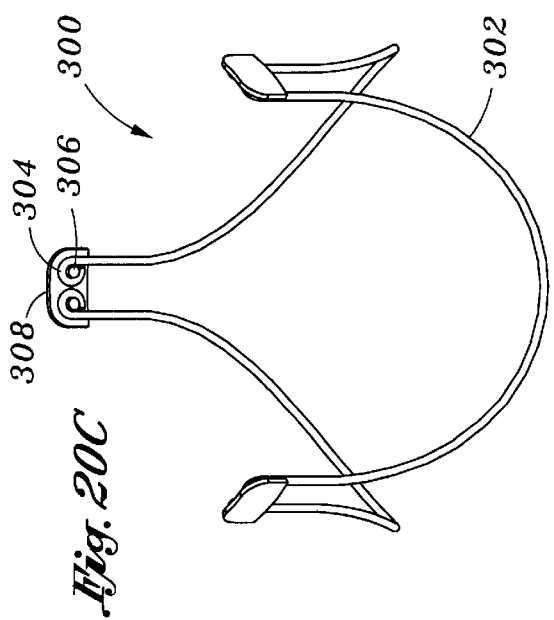

FIG. 20C illustrates a third alternative stent 300 suitable for use in a heart valve of the present invention. The stent 300 comprising three separate wires 302 terminating at circular commissure tips 304. Each of the commissure tips 304 is rotatably fastened around a pin 306 provided on a junction plate 308 common to adjacent wires 302. In this manner, the tips 304 remained located close to one another, while the cusps of the wires 302 can pivot in and out.

Figure 20D:
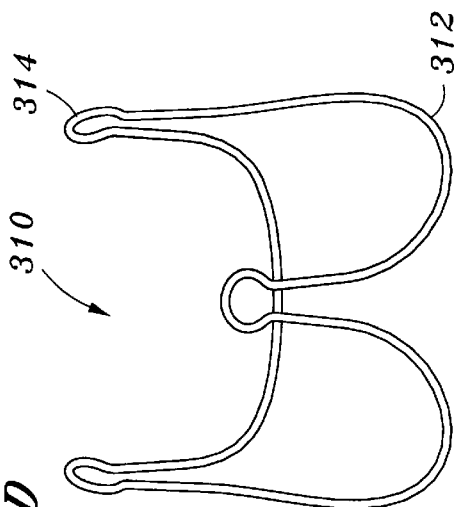
Figure 25:
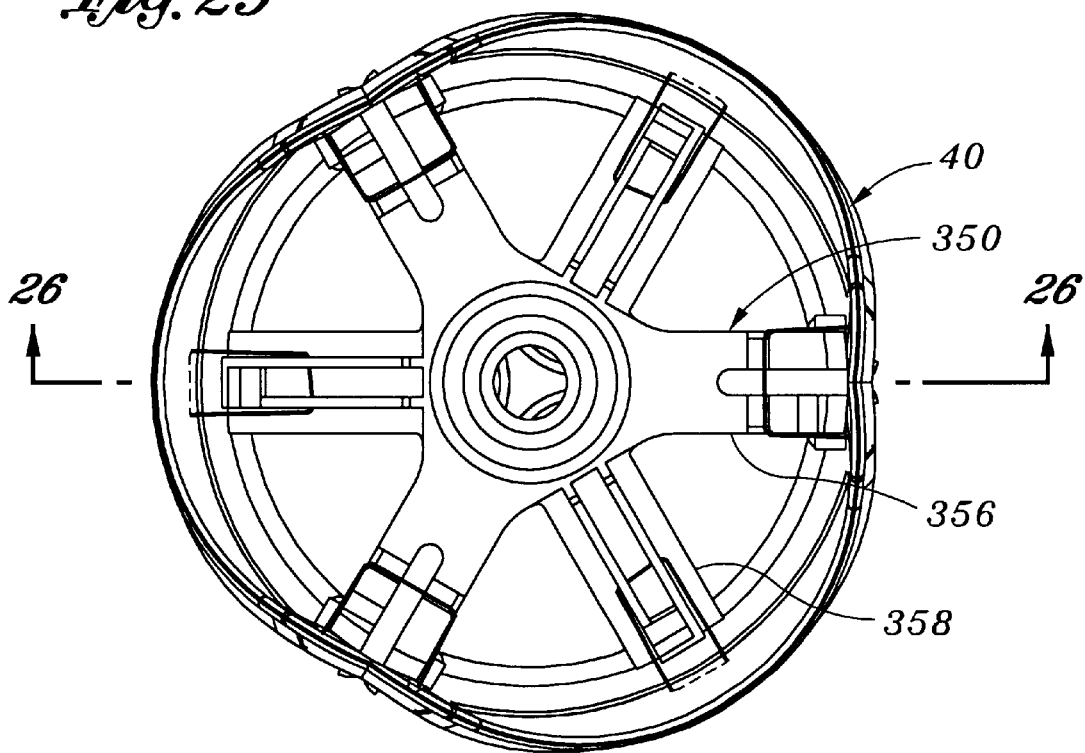
FIG. 25 is a top plan view of the holder coupled to the valve.

FIG. 20D illustrates a fourth alternative stent 310 suitable for use in a heart valve of the present invention. The stent 310 is made in one piece with a series of alternating cusps 312 and commissures 314. The commissures 314 comprising a nearly 360° bend in the stent 310 which permits each cusp 312 to easily flex with respect to the other cusps.

FIG. 20E illustrates a fifth alternative stent 320 suitable for use in a heart valve of the present invention. The stent 320 comprises three wire-like stent members 322, adjacent ones of which are joined together at commissure regions 324 by a U-shaped coupling 326 and a pair flexible sleeves 328.

FIG. 21 is a detail of one of the commissure regions 324 showing in hidden lines the adjacent ends of the coupling 326 and stent members 322. The couplings 326 are preferably sized with the same diameter as the stent members 322, and the sleeves 328 are tubular with a constant diameter lumen. The sleeves 328 may be made of silicone, or a flexible polymer such as polyurethane or the like. Other flexible interfaces such as sleeves 328 are contemplated, such as, for example, a single block of silicone into which the commissure regions 324 of the stent members 322 are molded.

FIG. 22 is a detailed view of a commissure region 330 of a still further alternative stent suitable for use in a heart valve of the present invention. The stent is made in one piece with adjacent cusps 332 being joined by a coil spring tip 334. Again, great flexibility is provided by the coil spring tips 334 to enable relative motion of the cusps 332. The amount of flexibility is selected as in any spring by varying the material, cross-sectional size and shape, and number of turns of the spring.

Valve Holder

FIGS. 23–26 illustrate a preferred holder 350 useful for implanting the flexible heart valve 40 of the present invention. As the heart valve 40 is relatively flexible, the holder 350 must provide adequate support to insure a stable platform for the surgeon to position the valve for attachment to the natural tissue. In other words, because the flexible prosthetic heart valve 40 of the present invention exhibits alternating cusps and commissures in a generally cylindrical configuration that are adapted to move radially in and out with respect to one another, the holder 350 desirably provides rigid structure for maintaining a fixed shape of the valve during implantation. In addition, the holder 350 must include structure to allow quick release from the valve 48 after the valve is implanted.

As seen in FIG. 23, the holder 350 comprises a proximal handle socket 352 having an inner bore 354 for receiving the distal end of a handle (not shown). The socket 352 may be provided with internal threads, or other such quick-release coupling structure to facilitate handle connection and disconnection. The holder 350 has three radially outwardly-directed commissure legs 356, and three outwardly and downwardly angled cusp legs 358. Consistent with the distribution of the cusps 150 and commissures 152 of the valve 40, the commissure legs 356 are oriented 120° apart, and the cusp legs 358 are oriented 120° apart, with the three commissure legs being offset with respect to the three cusp legs by 60°.

Figure 26:
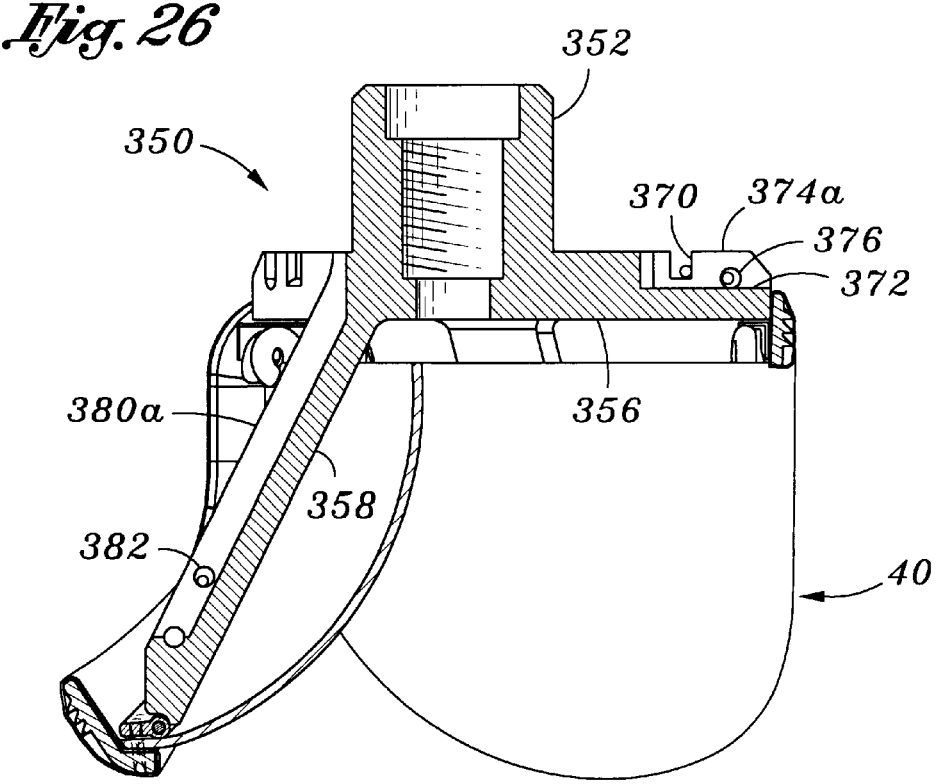
FIG. 26 is a cross-sectional view through the holder and valve, taken along line 26—26 of FIG. 25.

As seen in FIG. 24, each of the commissure legs 356 extends outward from the handle socket 352 into proximity with one of the valve commissures 152 and is secured thereto with an upper suture 360. Likewise, each of the cusp legs 358 extends outward and downward from the handle socket 352 into proximity with a midpoint of one of the valve cusps 150, and is secured thereto with a lower suture 362. The lower end of each cusp leg 358 includes a concavity for mating with the corresponding rod-like stent member 74, as seen in FIG. 26. In this manner, each of the cusps 150 and commissures 152 of the valve 40 is securely held in relation to the others, thus facilitating implantation by the surgeon.

Details of the commissure legs 356 will now being described with reference to FIGS. 23 and 26. Each commissure leg 356 extends outward from the handle socket 352 in a generally rectangular cross-section interrupted by an upwardly-facing inner notch 370 oriented cross-wise to the leg. And upwardly-facing radial channel 372 having a depth of approximately half of each commissure leg 356 extends from about the inner notch 370 to the outermost end of the leg. The inner notch 370 is not quite as deep as the channel 372, as seen in FIG. 26. The radial channel 372 divides the upper portion of each commissure leg 356 into two walls 374a, 374b. An eyehole 376 is formed in one of the walls 374a, and a corresponding outer notch 378 is formed in the other wall 374b aligned with the eyehole. The outer notch 378 is also not quite as deep as the channel 372.

With reference to FIGS. 24 and 26, the upper suture 360 is preferably tied to the eyehole 376 in the first wall 374a. The suture 360 then passes across the channel 372, through the outer notch 378, and is passed along the inner notch 370, again traversing the channel 372. The suture 368 is then passed through a suture-permeable portion of the valve commissure 152, such as through the connecting band 48. After passing through the commissure 152, the suture 360 is again looped through one or both of the notches 370, 378 and re-tied to the eyehole 376. By proper threading of the upper suture 360, each commissure 152 can be secured to the commissure leg 356 and easily released by inserting a scalpel blade into the radial channel 372 to sever the portions of the suture therein.

Details of each cusp leg 358 can be seen in FIGS. 23 and 26. A pair of longitudinal rails 380a, 380b are provided on the outer side of each cusp leg 358. Toward the lower end of the rails 380a,b, a pair of aligned eyeholes 382 provide anchoring locations for the lower suture 362. A scalpel guide or relief 384 is formed in one of the rails 380b. As seen in FIG. 24, the lower suture 362 extends downward from the eyeholes 382, passes through a suture-permeable portion of the cusp 150, and is then returned and secured to the eyeholes 382. The relief 384 exposes a portion of the lower suture 362 for severing by the surgeon using a scalpel blade. It will thus be understood that the holder 350 can be quickly released from the valve 40 by a series of six scalpel strokes, with each of the sutures 360, 362 remaining attached to the holder 350 and being withdrawn from the valve 40 as the holder is withdrawn.

Figure 27A:
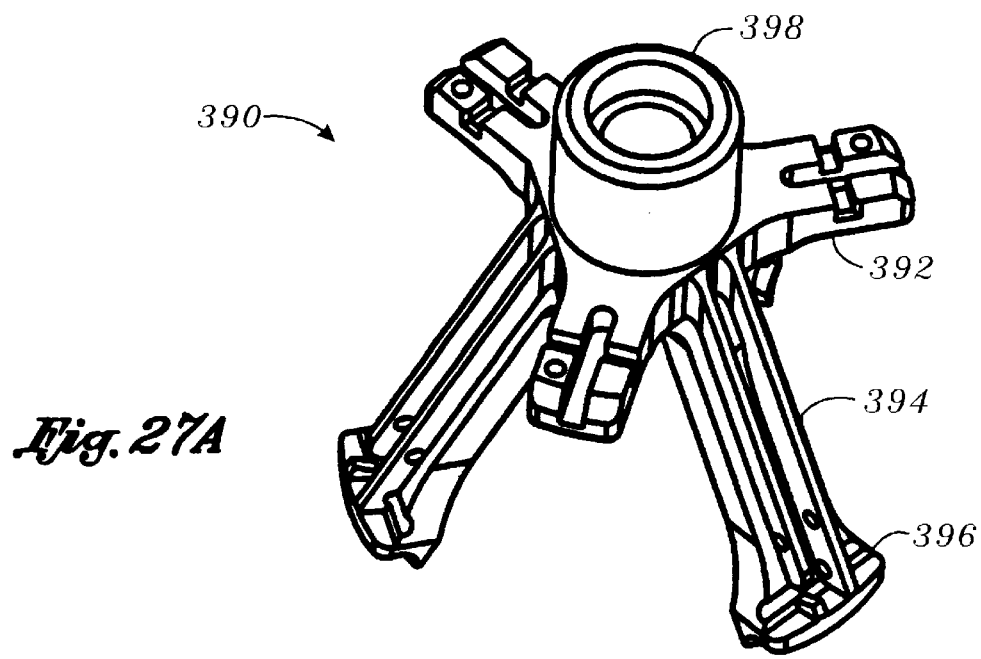
FIGS. 27A and 27B are perspective views of an alternative holder for the prosthetic heart valve of the present invention used during implantation of the valve.
Figure 27B:
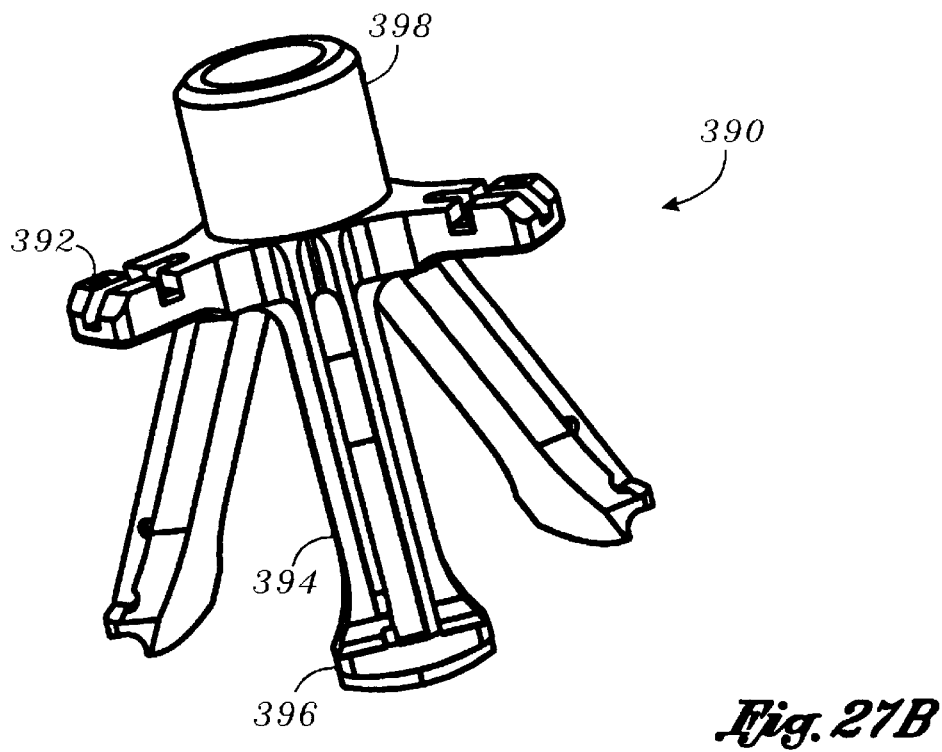

FIGS. 27A and 27B illustrate an alternative holder 390 useful for implanting the flexible heart valve 40 of the present invention. The holder 390 is substantially similar to the holder 350 described above, but the ends of each of a plurality of rigid legs for attaching to the valve cusps are flared, or, more precisely, each lower leg has a width from a hub to a terminal end that is greatest at the terminal end to provide more surface area to contact the corresponding valve cusp. That is, the holder 390 includes a plurality of upper legs 392 having a generally constant width, and a plurality of lower legs 394 having flared ends 396, the legs extending from a central hub 398. Again, the upper legs 392 extend radially outward to connect to the valve commissures 152, and the lower legs 394 angle radially outward and downward to connect to the valve cusps 150. The flared ends 396 impart greater stability to the flexible valve 40 during implantation, especially helping to prevent movement of the cusps 150. In addition, the legs 194 remain fairly narrow until the flared ends 396 to maintain good visibility through the spaces between the plurality of legs. That is, for example, the surgeon can continue to view the valve leaflets 42 between the legs as a check on valve orientation.

Independent Leaflets

A further aspect of the invention is a heart valve having three leaflets directly sutured to the aortic annulus wherein the commissures of adjacent leaflets are totally or partially independent, and may be connected during implant but will become independent thereafter. This gives the independent leaflets and juxtaposed commissures full freedom to move during systole and diastole, thus reducing the pressure gradient. For example, any of the stent assemblies described herein (such as, e.g., the stent assemblies of FIGS. 17–19) may include separate stent members initially coupled together with a permanent or bioresorbable fastener, the latter dissolving after a fairly short amount of time to permit independent movement of the leaflets. In addition, the present invention discloses an independent leaflet and implantation device that can replace a single defective leaflet, with the prosthetic leaflet functioning in conjunction with the remaining native leaflets.

One example of an independent leaflet 400 seen in FIGS. 28A and 28B includes a planar or three-dimensional body 402 defined by a coapting edge 404 and a fixation edge 406. The fixation edge 406 includes an arcuate cusp region 408 and a pair of commissure regions 410. The body 402 is attached along its fixation edge 406 to an arcuate flexible support 412 that preserves the shape of the fixation edge and provides a platform for attachment to the native tissue. FIG. 28B shows the leaflet 400 attached to a native annulus 422 adjacent a native leaflet 423.

The leaflet body 402 may be made from a biological material such as a porcine valve leaflet or a piece of bovine pericardium, chemically or physically treated to prevent immunological reaction and fatigue. Alternatively, the leaflet body 402 may be formed of a synthetic material such as a polymer or a woven fabric. The flexible support 412 is desirably made of a synthetic material, for example silicone or PTFE.

As mentioned previously, the independent leaflet 400 may be used with other such leaflets, preferably three total, that are attached directly to an ascending aorta and function together as a prosthetic valve. That is, as seen in FIG. 29A, adjacent flexible supports 412 may be attached at their juxtaposed commissure regions with a separate fastener 414, such as a clip. The clip 414 may be permanent or bioresorbable. Regardless of its longevity, the clips 414, when securing the leaflets 400 together, permit the leaflets to flex with respect to one another so as to allow the assembled valve to move in synch with the native tissue during the sytole/diastole cycle. This, in turn, reduces the pressure gradient through the valve. FIG. 29B illustrates an alternative fastener between independent leaflets in the form of a continuous scalloped wire or stent 416. Each leaflet 400 (either the leaflet body 402 directly or via the support 412) is attached to the scalloped stent 416 and thus functions together with the other leaflets in a prosthetic valve. The embodiment in FIG. 29B is similar to those previously described, wherein the scalloped stent 416 is highly flexible and permits both cusp and commissure movement. Again, however, the commissure regions 418 of the stent 416 may be bioresorbable to result in completely independent leaflets after a period of time in the body.

FIG. 30 is a perspective view of an exemplary independent leaflet measuring device 420 used to select the appropriate leaflet 400 according to the size and geometry of the native annulus 422. The device 420 includes a handle 424 and an arcuate leaflet sizer 426 that is sized and shaped to match the prosthetic leaflet. Two or more struts 428 may extend between the handle 424 and sizer 426 to improve stability in rotation and manipulation of the sizer. FIGS. 31A–31C are schematic views of a device 440 for automatically implanting an independent leaflet of the present invention, illustrating an articulated holder especially suited for minimally invasive environments. The device 440 includes a handle 442 connected to the independent leaflet 444 via a leaflet holder 446, comprising a plurality of movable struts 446. The struts 446 pivot or slide with respect to one another to convert the device from the low-profile configuration shown in FIG. 31A capable of passing through small apertures, to the full deployment configuration of FIG. 31C. The leaflet 444 may be attached to the leaflet holder 446 with sutures or the like. A plurality of staples 448 are provided extending outward from the leaflet fixation edge that pierce the native tissue and are deformed by a backing tool or assume a bent shape upon a temperature change. The final configuration is seen in FIG. 31C, and those of skill in the art will appreciate the ease of use of the separate leaflet implantation procedure. Once implanted, any structure connecting the leaflet 444 to the device 440 is severed, and the device removed.

FIGS. 32A–32C are schematic views of a still further exemplary implantation device for the independent leaflet embodiment. The device includes an anvil or backing portion 460 having a handle 462 and a plurality of fluid-carrying tubes 464 through which a cold or warm fluid can circulate, as seen by the arrows 466. The circulating fluid regulates the temperature of the tubes 464 during implantation. The device further includes a holder 470, similar to the holder 440 of FIG. 31A, to which an independent leaflet 472 is temporarily attached, such as with sutures 474. The fluid-carrying tubes 464 of the backing portion 460 is placed below the native annulus 476 while the leaflet holder 470 is maneuvered into position above the annulus. Opposite displacement of the backing portion 460 and holder 470 causes a plurality of staples 478 to pierce the annulus 476 and be deflected or otherwise curled by the tubes 464. If the staples 478 are shape memory alloy materials like Nitinol, the fluid circulating through the tubes 464 can be used to cause a temperature-induced shape change.

FIG. 33 is a cross-sectional view through one embodiment of an attachment structure for the independent leaflet embodiment. The structure includes staples 480 that extend outward from a leaflet fixation edge 482 through the native tissue 484, and curl or bend into a shape that prevents removal. The curling of the staples 480 may be accomplished using the device 460 (i.e., the backing portion 460 and holder 470) that provide a backing plate or anvil, or through a temperature change, such as when a shape memory material is used. In the illustrated embodiment, the staples 480 may include adjacent legs that curl at different lengths to accommodate one another. Exemplary dimension are shown in FIG. 33, with the width of the leaflet fixation edge 482 being about 9 mm, the length of one leg of each staple 480 being about 8 mm, and the length of one leg of each staple 480 being about 10 mm.

The present invention may be embodied in other specific forms without departing from its spirit or essential characteristics. The described embodiments are to be considered in all respects only as illustrative and not restrictive. In particular, though the flexible nature of the present heart valve has been described as being particularly suitable for use in the aortic position, the advantage of flexibility could equally apply to a valve implanted in other positions, such as the mitral position. The scope of the invention is, therefore, indicated by the appended claims rather than by the foregoing description. All changes which come within the meaning and range of equivalency of the claims are to be embraced within their scope.

What is claimed is:

1. A method of surgically repairing a heart valve having multiple native leaflets located in a native annulus of a heart, comprising the steps of:

providing an independent prosthetic leaflet; and, replacing a single native leaflet with the independent prosthetic leaflet;

wherein the replacing step comprises positioning the independent prosthetic leaflet in the native annulus such that the independent prosthetic leaflet functions in conjunction with the remaining native leaflets to regulate blood flow through the annulus.

2. The method of claim 1, wherein the independent leaflet comprises a flexible body having an arcuate fixation edge defined by a cusp region and two commissure regions, and a coapting edge between the two commissure regions, and a flexible support attached along the fixation edge.

3. The leaflet of claim 2, wherein the flexible body is a biomaterial and the support comprises a strip of synthetic material.

4. The leaflet of claim 3, wherein the flexible body is made of bovine pericardium.

5. The method of claim 1, wherein the replacing step further comprises passing a plurality of staples through the independent leaflet and the native annulus.

6. The method of claim 5 wherein the staples are made of a shape memory material, the method further comprising the step of regulating the temperature of the staples to induce a temperature-induced shape change in the staples that causes the staples to bend.

7. The method of claim 6, further comprising the steps of:

providing an implantation device having a fluid circulation path; and, regulating the temperature of the fluid to regulate the temperature of the staples.

8. The method of claim 5, further comprising the step of bending the staples with an anvil.

9. A method of surgically repairing a heart valve having multiple native leaflets located in a native annulus of a heart, comprising:

providing a plurality of individual prosthetic leaflets; and, replacing the native leaflets with the plurality of individual prosthetic leaflets;

wherein the replacing step comprises sequentially and independently attaching each independent prosthetic leaflet to the native annulus.

10. The method of claim 9 wherein the number of individual prosthetic leaflets corresponds to the number of native leaflets.

11. The method of claim 9, wherein each independent leaflet comprises a flexible body having an arcuate fixation edge defined by a cusp region and two commissure regions, and a coapting edge between the two commissure regions, and a flexible support attached along the fixation edge.

12. The leaflet of claim 11, wherein the flexible body is a biomaterial and the support comprises a strip of synthetic material.

13. The leaflet of claim 12, wherein the flexible body is made of bovine pericardium.

14. The method of claim 9, wherein the replacing step further comprises passing a plurality of staples through the independent leaflet and the native annulus.

15. The method of claim 14 wherein the staples are made of a shape memory material, the method further comprising the step of regulating the temperature of the staples to induce a temperature-induced shape change in the staples that causes the staples to bend.

16. The method of claim 15, further comprising the steps of:

providing an implantation device having a fluid circulation path; and, regulating the temperature of the fluid to regulate the temperature of the staples.

17. The method of claim 14, further comprising the step of bending the staples with an anvil.

18. A method of surgically repairing a heart valve having multiple native leaflets located in a native annulus of a heart, comprising:

removing one or more, but not all, of the native leaflets;

providing a number of independent prosthetic leaflets corresponding to the number of removed native leaflets;

replacing the removed native leaflets with individual prosthetic leaflets;

wherein the replacing step comprises sequentially and independently attaching each independent prosthetic leaflet to the native annulus; and positioning the independent prosthetic leaflets in the annulus adjacent the remaining native leaflets such that the independent prosthetic leaflets function in conjunction with the remaining native leaflets to regulate blood flow through the annulus.

19. The method of claim 18, wherein each independent leaflet comprises a flexible body having an arcuate fixation edge defined by a cusp region and two commissure regions, and a coapting edge between the two commissure regions, and a flexible support attached along the fixation edge.

20. The leaflet of claim 19, wherein the flexible body is a biomaterial and the support comprises a strip of synthetic material.

21. The leaflet of claim 20, wherein the flexible body is made of bovine pericardium.

22. The method of claim 18, wherein the replacing step further comprises passing a plurality of staples through the independent leaflet and the native annulus.

23. The method of claim 22 wherein the staples are made of a shape memory material, the method further comprising the step of regulating the temperature of the staples to induce a temperature-induced shape change in the staples that causes the staples to bend.

24. The method of claim 23, further comprising the steps of:

providing an implantation device having a fluid circulation path; and, regulating the temperature of the fluid to regulate the temperature of the staples.

25. The method of claim 22, further comprising the step of bending the staples with an anvil.

* * * * *